(12) United States Patent
Kashefhaghighi et al.

(10) Patent No.: US 12,073,922 B2
(45) Date of Patent: Aug. 27, 2024

(54) DEEP LEARNING-BASED FRAMEWORK FOR IDENTIFYING SEQUENCE PATTERNS THAT CAUSE SEQUENCE-SPECIFIC ERRORS (SSEs)

(71) Applicant: Illumina, Inc., San Diego, CA (US)

(72) Inventors: Dorna Kashefhaghighi, Menlo Park, CA (US); Amirali Kia, San Mateo, CA (US); Kai-How Farh, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 1297 days.

(21) Appl. No.: 16/505,100

(22) Filed: Jul. 8, 2019

(65) Prior Publication Data

US 2020/0251183 A1    Aug. 6, 2020

Related U.S. Application Data

(60) Provisional application No. 62/696,699, filed on Jul. 11, 2018.

(30) Foreign Application Priority Data

Aug. 16, 2018    (NL) .................................... 2021473

(51) Int. Cl.
*G16B 40/00*    (2019.01)
*G06N 3/04*    (2023.01)
(Continued)

(52) U.S. Cl.
CPC ............... *G16B 40/00* (2019.02); *G06N 3/04* (2013.01); *G16B 20/20* (2019.02); *G16B 30/10* (2019.02)

(58) Field of Classification Search
CPC ........ G16B 40/00; G16B 20/20; G16B 30/10; G16B 40/20; G16B 30/00; G06N 3/04; G06N 3/0454
See application file for complete search history.

(56) References Cited

U.S. PATENT DOCUMENTS

| 5,641,658 A | 6/1997 | Adams et al. |
| 7,057,026 B2 | 6/2006 | Barnes et al. |

(Continued)

FOREIGN PATENT DOCUMENTS

| RU | 2309457 C1 | 10/2007 |
| WO | 9106678 A1 | 5/1991 |

(Continued)

OTHER PUBLICATIONS

Shin, Sunguk, and Joonhong Park. "Characterization of sequence-specific errors in various next-generation sequencing systems." Molecular BioSystems 12.3 (2016): 914-922. (Year: 2016).*

(Continued)

*Primary Examiner* — Russell S Negin
*Assistant Examiner* — Guozhen Liu
(74) *Attorney, Agent, or Firm* — Keller Preece PLLC

(57) ABSTRACT

The technology disclosed presents a deep learning-based framework, which identifies sequence patterns that cause sequence-specific errors (SSEs). Systems and methods train a variant filter on large-scale variant data to learn causal dependencies between sequence patterns and false variant calls. The variant filter has a hierarchical structure built on deep neural networks such as convolutional neural networks and fully-connected neural networks. Systems and methods implement a simulation that uses the variant filter to test known sequence patterns for their effect on variant filtering. The premise of the simulation is as follows: when a pair of a repeat pattern under test and a called variant is fed to the variant filter as part of a simulated input sequence and the variant filter classifies the called variant as a false variant call, then the repeat pattern is considered to have caused the false variant call and identified as SSE-causing.

23 Claims, 21 Drawing Sheets

(51) Int. Cl.
  *G16B 20/20* (2019.01)
  *G16B 30/10* (2019.01)
  *G06N 3/045* (2023.01)
  *G06N 3/082* (2023.01)

(56) References Cited

U.S. PATENT DOCUMENTS

| | | | |
|---|---|---|---|
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2007/0099208 | A1 | 5/2007 | Ormanac et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0108082 | A1 | 5/2008 | Rank et al. |
| 2008/0280773 | A1 | 11/2008 | Fedurco et al. |
| 2009/0088327 | A1 | 4/2009 | Rigatti et al. |
| 2013/0085681 | A1 | 4/2013 | Deciu et al. |
| 2013/0296175 | A1 | 11/2013 | Rafnar et al. |
| 2014/0180986 | A1 | 6/2014 | Hinton et al. |
| 2016/0085910 | A1 | 3/2016 | Bruand et al. |
| 2017/0076038 | A1 | 3/2017 | Rabinowitz et al. |
| 2018/0030528 | A1 | 2/2018 | Van Den Boom et al. |

FOREIGN PATENT DOCUMENTS

| | | |
|---|---|---|
| WO | 2004018497 A3 | 6/2004 |
| WO | 2007010252 A1 | 1/2007 |
| WO | 2008041002 A3 | 6/2008 |
| WO | 2007123744 A3 | 11/2008 |
| WO | 2014039556 A1 | 3/2014 |
| WO | 2014142831 A1 | 9/2014 |
| WO | 2020014280 A1 | 1/2020 |

OTHER PUBLICATIONS

Oord, Dieleman et. al., WAVENET: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et al., Highway Networks, 2015.
Huang et. al., Densely Connected Convolutional Networks, 2017.
Szegedy et. al., Going Deeper with Convolutions, dated 2014, 12 pages.
Ioffe et al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
Goodfellow et. al., Convolutional Networks, Deep Learning, MIT Press, 2016.
Gu, et. al., "Recent Advances in Convolutional Neural Networks", Jan. 5, 2017, 37pgs.
Srivastava, Dropout A Simple Way to Prevent Neural Networks from Overfitting, 2014, 30 pages.
Dijke, "Convolutional Neural Networks for Regulatory Genomics", Jun. 17, 2017, Universiteit Leiden Opleiding Informatica, Master's Thesis, Leiden Institute of Advanced Computer Science (LIACS), Leiden University, The Netherlands, pp. 1-58.

Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet [URL: https://media.nature.com/original/nature-assets/nature/journal/v456/n7218/extref/nature07517-s1.pdf ].
Illumina, Pisces, Github, retrieved on Mar. 9, 2022, 5 pages. Retrieved from the internet [URL: https://github.com/Illumina/Pisces ].
Dunn et al., Pisces: An Accurate and Versatile Variant Caller for Somatic and Germline Next-Generation Sequencing Data, dated Mar. 29, 2018, 3 pages.
Stromberg et al., Nirvana: Clinical Grade Variant Annotator, ACM-BCB 2017, Aug. 20-23, 2017, 1 page.
Illumina, Nirvana Wiki, Github, 3 pages. Retrieved on Mar. 9, 2022. Retrieved from the internet [URL: https://github.com/Illumina/Nirvana/wiki ].
Keras, Layers, Documentation, 4 pages. Retrieved on Mar. 9, 2022. Retrieved from the internet [URL: https://keras.io/layers/about-keras-layers/ ].
Kundajelab, DeepLIFT—Deep Learning Important Features, Github, 16 pages. Retrieved on Mar. 9, 2022. Retrieved from the internet [URL: http://github.com/kundajelab/deeplift ].
Anonymous, Details for Implementing DeepLIFT and Saliency Map, Supplemental Material, dated Oct. 5, 2017, 5 pages.
NL 2021473—Search Report and Written Opinion, dated May 3, 2019, 13 pages.
CA 3064226—Notice of Allowance, dated Jan. 13, 2022, 1 page.
IL 271213—Response to Notice Before Allowance dated Apr. 15, 2021, filed Aug. 4, 2021, 9 pages.
IL 271213—Notice of Acceptance, dated Aug. 23, 2021, 5 pages.
KR 10-2019-7036426—Response to First Office Action dated Apr. 29, 2021, filed Jul. 29, 2021, 14 pages.
KR 10-2019-7036426—Notice of Allowance, dated Dec. 3, 2021, 3 pages.
RU 2019139413(077526)—Decision to Grant, dated Jan. 26, 2021, 18 pages.
ZA 201908149—Voluntary Amendments, dated Jun. 14, 2021, 11 pages.
Poplin et al., A universal SNP and small-indel variant caller using deep neural networks, bioRxiv, dated Mar. 20, 2020, 10 pages.
Treangen et al., Repetitive DNA and next-generation sequencing: computational challenges and solutions, Nature Reviews Genetics, dated Nov. 29, 2011, vol. 13, No. 1, pp. 36-46.
Cao, et al., Sequencing technologies and tools for short tandem repeat variation detection, Briefings in Bioinformatics, dated Feb. 6, 2014, vol. 16, Issue 2, pp. 193-204.
Lizardi et al., Mutation detection and single-molecule counting using isothermal rolling-circle amplification, Nature Genetics, vol. 19, pp. 225-232, dated Jul. 1998.
Office Action as received in Australian Application 2019272065 dated Jul. 4, 2022.
Office Action as received in Canadian Application 3064226 dated Sep. 20, 2022.
Notice of Acceptance as received in Israeli Application 28827621 dated Jun. 26, 2022.
Notice of Allowance as received in Korean Application 10-2022-7007154 dated Jun. 27, 2022.
Notice of Allowance as received in Mexican Application 2019015567 dated Apr. 26, 2022.
Office Action as received in New Zealand application 759884 dated Jan. 20, 2022.
Notice of Allowance as received South African application 201908149 dated May 29, 2022.
Schirmer, Melanie, et al. "Illumina error profiles: resolving fine-scale variation in metagenomic sequencing data", BMC bioinformatics 17.1, Mar. 11, 2016, 15 pages.
Allhoff et al., "Discovering motifs that induce sequencing errors", BMC bioinformatics, vol. 14. No. 5. BioMed Central, Apr. 2013, 10 pages.
PCT/US2019/041078—International Search Report and Written Opinion dated Oct. 7, 2019, 16 pages.

(56) References Cited

OTHER PUBLICATIONS

Ravasio et al., "GARFIELD-NGS: Genomic vARiants Filtering by deep Learning moDels in NGS," Bioinformatics 34, No. 17 (2018): 3038-3040.
Poplin et al., "Creating a universal SNP and small indel variant caller with deep neural networks," BioRxiv (2016), 13 pages.
O'Fallon et al., "A support vector machine for identification of single-nucleotide polymorphisms from next-generation sequencing data," Bioinformatics 29, No. 11 (2013), pp. 1361-1366.
PCT/US2019/041078—Article 34 Amendments filed Dec. 18, 2019, 23 pages.
Anchantin et al., "Deep motif dashboard: Visualizing and understanding genomic sequences using deep neural networks." In Pacific Symposium on Biocomputing 2017, pp. 254-265, 2017.
Nakamura et al., "Sequence-specific error profile of Illumina sequencers." Nucleic acids research 39, No. 13 (2011): e90-e90, 13 pages.
Selvaraju et al., "Grad-cam: Visual explanations from deep networks via gradient-based localization." In Proceedings of the IEEE international conference on computer vision, 24 pages, Mar. 21, 2017.
Shrikumar et al., "Not just a black box: Learning important features through propagating activation differences." arXiv preprint arXiv:1605.01713 (2016), 6 pages.
Sundararajan et al., "Axiomatic attribution for deep networks." In Proceedings of the 34th International Conference on Machine Learning—vol. 70, 11 pages. PMLR. org, 2017.
Zintgraf et al., "Visualizing deep neural network decisions: Prediction difference analysis." arXiv preprint arXiv:1702.04595 (2017), 12 pages.
Shrikumar et al., "Learning important features through propagating activation differences." In Proceedings of the 34th International Conference on Machine Learning—vol. 70, 9 pages. JMLR. org, 2017.
AU 2019272065—First Office Action dated Feb. 20, 2020, 2 pages.
PCT/US2019/041078—2nd Written Opinion of the International Preliminary Examining Authority dated Feb. 12, 2020, 5 pages.
PCT/US2019/041078—Article 34 Amendments filed Apr. 10, 2020, 16 pages.
Selvararaju et al, "Grad-CAM: Visual Explanations from Deep Networks via Gradient-based Localization", http://gradcam.cloudcv.org, arXiv:1610.02391v3 [cs.CV] Mar. 21, 2017, 24 pages.
DePristo, et al, "DeepVariant: Highly Accurate Genomes With Deep Neural Networks", Crossposted on the Google Open Source Blog, Dec. 4, 2017.
PCT/US2019/041078—International Preliminary Report of Patentability dated Aug. 13, 2020, 9 pages.
AU 2019272065—Response to First Office Action dated Feb. 5, 2021, 156 pages.
AU 2019272065—Notice of Acceptance dated Feb. 8, 2021, 3 pages.
CA 3,064,226—First Office Action mailed Jun. 15, 2020, 5 pages.
CA 3,064,226—Response to First Office Action mailed Oct. 15, 2020, 81 pages.
CN 201980003258.8—Voluntary Amendment filed Jul. 6, 2020, 19 pages with English translation.
EP 19742664.6—Rule 161(2) & 162 communication mailed Jan. 31, 2020, 3 pages.
EP 19742664.6—Response to Rule 161(2) & 162 communication mailed Jan. 31, 2020, filed Aug. 10, 2020, 21 pages.
JP 2019-567519 Notice of Allowance, dated Sep. 28, 2020, 3 pages.
RU 2019139413 Decision to Grant, dated Jan. 26, 2021, 18 pages.
CA 3064226 Second Office Action, dated Jan. 25, 2021, 3 pages.
IL 271213 Notice Before Examination, dated Sep. 29, 2020, 2 pages.
IL 271213 Response to Notice Before Examination, response dated Jan. 31, 2021, 243 pages.
IL 271213 Notice Before Allowance, dated Apr. 12, 2021, 7 pages.
IN 201917050606 First Office Action, dated Mar. 9, 2021, 10 pages.
KR 10-2019-7036426 First Office Action, dated Apr. 29, 2021, 5 pages.
IN 201917050606—Response to First Office Action, dated Sep. 9, 2021, 25 pages.
Saunders, Strelka accurate somatic small variant calling from sequenced tumornormal sample pairs, dated 2012, 7 pages.
Saunders et. al., Supplementary Methods for Strelka Accurate somatic small variant calling, Mar. 28, 2012, 4 pages.
Kim et. al., Strelka 2 Fast and accurate variant calling for clinical sequencing applications, Sep. 23, 2017, 19 pages.
Strelka2 germline and somatic small variant caller Illumina, GitHub, Jan. 10, 2019, 3 pages.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et al., MobileNetV2: Inverted Residuals and Linear Bottlenecks, 2018.
Qin et. al., FD-MobileNet: Improved MobileNet with a Fast Downsampling Strategy, 2018.

* cited by examiner

FIG. 5

DEEP LEARNING-BASED FRAMEWORK FOR IDENTIFYING SEQUENCE PATTERNS THAT CAUSE SEQUENCE-SPECIFIC ERRORS (SSEs)

PRIORITY APPLICATION

This application claims priority to or the benefit of the following applications: U.S. Provisional Patent Application No. 62/696,699, entitled "DEEP LEARNING-BASED FRAMEWORK FOR IDENTIFYING SEQUENCE PATTERNS THAT CAUSE SEQUENCE-SPECIFIC ERRORS (SSEs)," filed on Jul. 11, 2018;

Netherlands Application No. 2021473, entitled "DEEP LEARNING-BASED FRAMEWORK FOR IDENTIFYING SEQUENCE PATTERNS THAT CAUSE SEQUENCE-SPECIFIC ERRORS (SSEs)," filed on Aug. 16, 2018.

The priority applications are hereby incorporated by reference for all purposes.

INCORPORATIONS

The following are incorporated by reference for all purposes as if fully set forth herein:

Strelka™ application by Illumina Inc. hosted at github.com/Illumina/strelka and described in the article T Saunders, Christopher & Wong, Wendy & Swamy, Sajani & Becq, Jennifer & J Murray, Lisa & Cheetham, Keira. (2012). Strelka: Accurate somatic small-variant calling from sequenced tumor-normal sample pairs. Bioinformatics (Oxford, England). 28. 1811-7;

Strelka2™ application by Illumina Inc. hosted at github.com/Illumina/strelka and described in the article Kim, S., Scheffler, K., Halpern, A. L., Bekritsky, M. A., Noh, E., Kallberg, M., Chen, X., Beyter, D., Krusche, P., and Saunders, C. T. (2017);

A. van den Oord, S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv:1702.07825, 2017;

F. Yu and V. Koltun, "MULTI-SCALE CONTEXT AGGREGATION BY DILATED CONVOLUTIONS," arXiv:1511.07122, 2016;

K. He, X. Zhang, S. Ren, and J. Sun, "DEEP RESIDUAL LEARNING FOR IMAGE RECOGNITION," arXiv:1512.03385, 2015;

R. K. Srivastava, K. Greff, and J. Schmidhuber, "HIGHWAY NETWORKS," arXiv: 1505.00387, 2015;

G. Huang, Z. Liu, L. van der Maaten and K. Q. Weinberger, "DENSELY CONNECTED CONVOLUTIONAL NETWORKS," arXiv:1608.06993, 2017;

C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

Srivastava, Nitish, Hinton, Geoffrey, Krizhevsky, Alex, Sutskever, Ilya, and Salakhutdinov, Ruslan, "DROPOUT: A SIMPLE WAY TO PREVENT NEURAL NETWORKS FROM OVERFITTING," The Journal of Machine Learning Research, 15 (1):1929-1958, 2014;

J. M. Wolterink, T. Leiner, M. A. Viergever, and I. Išgum, "DILATED CONVOLUTIONAL NEURAL NETWORKS FOR CARDIOVASCULAR MR SEGMENTATION IN CONGENITAL HEART DISEASE," arXiv: 1704.03669, 2017;

L. C. Piqueras, "AUTOREGRESSIVE MODEL BASED ON A DEEP CONVOLUTIONAL NEURAL NETWORK FOR AUDIO GENERATION," Tampere University of Technology, 2016;

J. Wu, "Introduction to Convolutional Neural Networks," Nanjing University, 2017;

I. J. Goodfellow, D. Warde-Farley, M. Mirza, A. Courville, and Y. Bengio, "CONVOLUTIONAL NETWORKS", Deep Learning, MIT Press, 2016;

J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv: 1512.07108, 2017;

M. Lin, Q. Chen, and S. Yan, "Network in Network," in Proc. of ICLR, 2014;

L. Sifre, "Rigid-motion Scattering for Image Classification, Ph.D. thesis, 2014;

L. Sifre and S. Mallat, "Rotation, Scaling and Deformation Invariant Scattering for Texture Discrimination," in Proc. of CVPR, 2013;

F. Chollet, "Xception: Deep Learning with Depthwise Separable Convolutions," in Proc. of CVPR, 2017;

X. Zhang, X. Zhou, M. Lin, and J. Sun, "ShuffleNet: An Extremely Efficient Convolutional Neural Network for Mobile Devices," in arXiv:1707.01083, 2017;

K. He, X. Zhang, S. Ren, and J. Sun, "Deep Residual Learning for Image Recognition," in Proc. of CVPR, 2016;

S. Xie, R. Girshick, P. Dollar, Z. Tu, and K. He, "Aggregated Residual Transformations for Deep Neural Networks," in Proc. of CVPR, 2017;

A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017;

M. Sandler, A. Howard, M. Zhu, A. Zhmoginov, and L. Chen, "MobileNetV2: Inverted Residuals and Linear Bottlenecks," in arXiv:1801.04381v3, 2018;

Z. Qin, Z. Zhang, X. Chen, and Y. Peng, "FD-MobileNet: Improved MobileNet with a Fast Downsampling Strategy," in arXiv:1802.03750, 2018;

PCT International Patent Application No. PCT/US17/61554, titled "Validation Methods and Systems for Sequence Variant Calls", filed on Nov. 14, 2017;

U.S. Provisional Patent Application No. 62/447,076, titled "Validation Methods and Systems for Sequence Variant Calls", filed on Jan. 17, 2017;

U.S. Provisional Patent Application No. 62/422,841, titled "Methods and Systems to Improve Accuracy in Variant Calling", filed on Nov. 16, 2016; and N. ten DIJKE, "Convolutional Neural Networks for Regulatory Genomics," Master's Thesis, Universiteit Leiden Opleiding Informatica, 17 Jun. 2017.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as convolutional neural networks (CNNs) and fully-connected neural networks (FCNNs) for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Next-generation sequencing has made large amounts of sequenced data available for variant filtering. Sequenced data are highly correlated and have complex interdependencies, which has hindered the application of traditional classifiers like support vector machine to the variant filtering task. Advanced classifiers that are capable of extracting high-level features from sequenced data are thus desired.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework that associates sequence patterns with sequencing errors.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 1 includes modules such as a variant filter, a simulator, and an analyzer. FIG. 1 also includes databases that store overlaid samples, nucleotide sequences, and repeat patterns.

FIG. 5 shows one implementation of one-hot encoding used to encode the overlaid sample that has a called variant at a target position flanked by 20-50 bases on each side.

DETAILED DESCRIPTION

Figure 1:
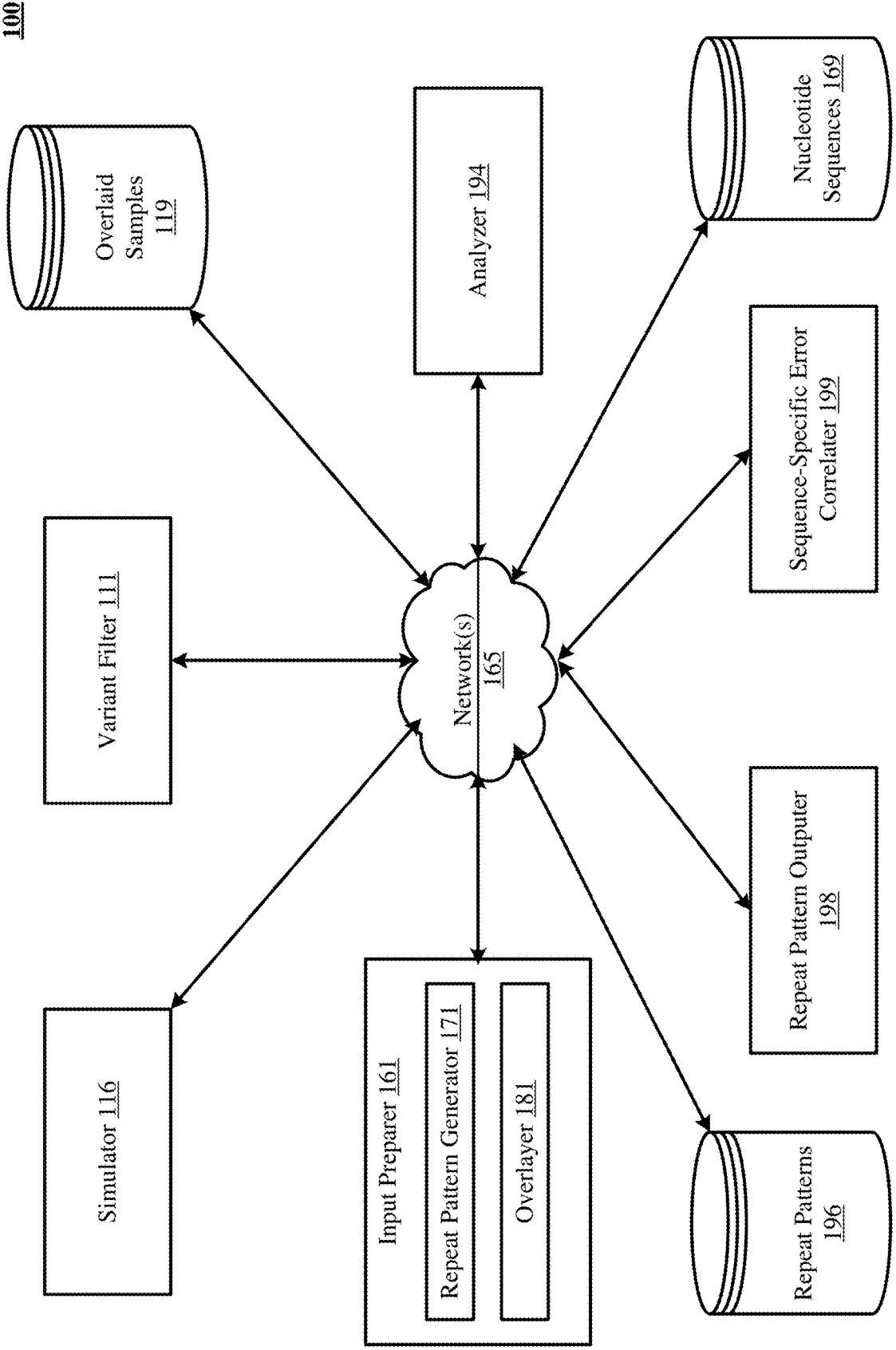
FIG. 1 is a block diagram that shows various aspects of DeepPOLY, a deep learning-based framework for identifying sequence patterns that cause sequence-specific errors (SSEs).

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

INTRODUCTION

Sequence-specific errors (SSEs) are base calling errors caused by specific sequence patterns. For example, the sequence patterns 'GGC' and 'GGCNG' and their inverted repeats have been found to cause large amounts of miscalls. SSEs lead to assembly gaps and mapping artifacts. Also, since any miscall can be mistaken for a variant, SSEs result in false variant calls and are a major obstacle to accurate variant calling.

We disclose a deep learning-based framework, DeepPOLY, which identifies sequence patterns that cause SSEs. DeepPOLY trains a variant filter on large-scale variant data to learn causal dependencies between sequence patterns and false variant calls. The variant filter has a hierarchical structure built on deep neural networks that evaluate an input sequence at multiple spatial scales and perform variant filtering, i.e., predict whether a called variant in the input sequence is a true variant call or a false variant call. The large-scale variant data includes pedigree variants, of which inherited variants are used as training examples of true variant calls and de novo variants observed in only one child are used as training examples of false variant calls. In some implementations, at least some of the de novo variants observed in only one child are used as training examples of true variant calls.

During training, parameters of the deep neural networks are optimized to maximize filtering accuracy using a gradient descent approach. The resulting variant filter learns to associate false variant calls with sequence patterns in the input sequences.

DeepPOLY then implements a simulation that uses the variant filter to test known sequence patterns for their effect on variant filtering. The known sequence patterns are repeat patterns (or copolymers) that differ in base composition, pattern length, and repeat factor. The repeat patterns are tested at varying offsets from the called variants.

The premise of the simulation is as follows: when a pair of a repeat pattern under test and a called variant is fed to the variant filter as part of a simulated input sequence and the variant filter classifies the called variant as a false variant call, then the repeat pattern is considered to have caused the false variant call and identified as SSE-causing. Under this premise, DeepPOLY tests hundreds and thousands of repeat patterns to identify which ones are SSE-causing, with offset sensitivity.

DeepPOLY also discovers naturally occurring sequence patterns that cause SSEs by processing naturally occurring input sequences through the variant filter and analyzing parameter activations of the deep neural networks during the processing. Those sequence patterns are identified as SSE-causing for which the input neurons of the deep neural networks produce the highest parameter activations and the output neurons produce a false variant call classification.

DeepPOLY confirms previously known SSE-causing sequence patterns and reports new more specific ones.

DeepPOLY is agnostic of the underlying sequencing chemistry, sequencing platform, and sequencing polymerases and can produce comprehensive profiles of SSE-causing sequence patterns for different sequencing chemistries, sequencing platforms, and sequencing polymerases. These profiles can be used to improve the sequencing chemistries, build higher quality sequencing platforms, and create different sequencing polymerases. They can also be used to recalculate base call quality scores and to improve variant calling accuracy.

The variant filter has two deep neural networks: a convolutional neural network (CNN) followed by a fully-connected neural network (FCNN). A repeat pattern under test is overlaid on a nucleotide sequence to produce an overlaid sample. The overlaid sample has a called variant at a target position flanked by 20-50 bases on each side. We regard the overlaid sample as an image with multiple channels that numerically encode the four types of bases, A, C, G, and T. The overlaid sample, spanning the called variant, is one-hot encoded to conserve the position-specific information of each individual base in the overlaid sample.

The convolutional neural network receives the one-hot overlaid sample because it is capable of preserving the spatial locality relationships within the overlaid sample. The convolutional neural network processes the overlaid sample through multiple convolution layers and produces one or more intermediate convolved features. The convolution layers utilize convolution filters to detect sequence patterns within the overlaid sample. The convolution filters act as motif detectors that scan the overlaid sample for low-level motifs and produce signals of different strengths depending on the underlying sequence patterns. The convolution filters are automatically learned after training on hundreds and thousands of training examples of true and false variant calls.

The fully-connected neural network then processes the intermediate convolved features through multiple fully-connected layers. The densely connected neurons of the fully-connected layers detect high-level sequence patterns encoded in the convolved features. Finally, a classification layer of the fully-connected neural network outputs probabilities for the called variant being a true variant call or a false variant call.

In addition to using dropout, pairs of batch normalization and rectified linear unit nonlinearity are interspersed between the convolutional layers and the fully-connected layers to enhance learning rates and reduce overfitting.

Terminology

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

A base refers to a nucleotide base or nucleotide, A (adenine), C (cytosine), T (thymine), or G (guanine).

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-20 inversely proportional to the probability that a single sequenced base is correct. For example, a T base call with Q of 20 is considered likely correct with a confidence P-value of 0.01. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

DeepPOLY

We describe DeepPOLY, a deep learning-based framework for identifying sequence patterns that cause sequence-specific errors (SSEs). The system and processes are described with reference to FIG. 1. Because FIG. 1 is an architectural diagram, certain details are intentionally omitted to improve the clarity of the description. The discussion of FIG. 1 is organized as follows. First, the modules of the figure are introduced, followed by their interconnections. Then, the use of the modules is described in greater detail.

FIG. 1 includes the system 100. The system 100 includes a variant filter 111 (also referred to herein as a variant filter subsystem), an input preparer 161 (also referred to herein as an input preparation subsystem), a simulator 116 (also referred to herein as a simulation subsystem), an analyzer 194 (also referred to herein as an analysis subsystem), a repeat patterns database 196, a nucleotide sequences database 169, an overlaid samples database 119, and a repeat pattern outputer 198 (also referred to herein as a repeat pattern output subsystem).

The processing engines and databases of FIG. 1, designated as modules, can be implemented in hardware or software, and need not be divided up in precisely the same blocks as shown in FIG. 1. Some of the modules can also be implemented on different processors, computers, or servers, or spread among a number of different processors, computers, or servers. In addition, it will be appreciated that some of the modules can be combined, operated in parallel or in a different sequence than that shown in FIG. 1 without affecting the functions achieved. The modules in FIG. 1 can also be thought of as flowchart steps in a method. A module also need not necessarily have all its code disposed contiguously in memory; some parts of the code can be separated from other parts of the code with code from other modules or other functions disposed in between.

The interconnections of the modules of environment 100 are now described. The network(s) 114 couples the processing engines and the databases, all in communication with each other (indicated by solid double-arrowed lines). The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX. Additionally, a variety of authorization and authentication techniques, such as username/password, Open Authorization (OAuth), Kerberos, SecureID, digital certificates and more, can be used to secure the communications.

Sequencing Process

Implementations set forth herein may be applicable to analyzing nucleic acid sequences to identify sequence variations. Implementations may be used to analyze potential variants/alleles of a genetic position/locus and determine a genotype of the genetic locus or, in other words, provide a genotype call for the locus. By way of example, nucleic acid sequences may be analyzed in accordance with the methods and systems described in US Patent Application Publication No. 2016/0085910 and US Patent Application Publication No. 2013/0296175, the complete subject matter of which are expressly incorporated by reference herein in their entirety.

In one implementation, a sequencing process includes receiving a sample that includes or is suspected of including nucleic acids, such as DNA. The sample may be from a known or unknown source, such as an animal (e.g., human), plant, bacteria, or fungus. The sample may be taken directly from the source. For instance, blood or saliva may be taken directly from an individual. Alternatively, the sample may not be obtained directly from the source. Then, one or more processors direct the system to prepare the sample for sequencing. The preparation may include removing extraneous material and/or isolating certain material (e.g., DNA). The biological sample may be prepared to include features for a particular assay. For example, the biological sample may be prepared for sequencing-by-synthesis (SBS). In certain implementations, the preparing may include amplification of certain regions of a genome. For instance, the preparing may include amplifying predetermined genetic loci that are known to include STRs and/or SNPs. The genetic loci may be amplified using predetermined primer sequences.

Next, the one or more processors direct the system to sequence the sample. The sequencing may be performed through a variety of known sequencing protocols. In particular implementations, the sequencing includes SBS. In SBS, a plurality of fluorescently-labeled nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders.

The nucleic acids can be prepared such that they comprise a known primer sequence that is adjacent to an unknown target sequence. To initiate the first SBS sequencing cycle, one or more differently labeled nucleotides, and DNA polymerase, etc., can be flowed into/through the flow cell by a fluid flow subsystem. Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g., A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection operations can be repeated several times to complete a sequencing run. Example sequencing methods are described, for example, in Bentley et al., Nature 456:53-59 (2008), International Publication No. WO 04/018497; U.S. Pat. No. 7,057,026; International Publication No. WO 91/06678; International Publication No. WO 07/123744; U.S. Pat. Nos. 7,329,492; 7,211,414; 7,315,019; 7,405,281, and U.S. Patent Application Publication No. 2008/0108082, each of which is incorporated herein by reference.

In some implementations, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Application Publication No. 2002/0055100; U.S. Pat. No. 7,115,400; U.S. Patent Application Publication No. 2004/0096853; U.S. Patent Application Publication No. 2004/0002090; U.S. Patent Application Publication No. 2007/0128624; and U.S. Patent Application Publication No. 2008/0009420, each of which is incorporated herein by reference in its entirety. Another useful method for amplifying nucleic acids on a surface is rolling circle amplification (RCA), for example, as described in Lizardi et al., Nat. Genet. 19:225-232 (1998) and U.S. Patent Application Publication No. 2007/0099208 A1, each of which is incorporated herein by reference.

One example SBS protocol exploits modified nucleotides having removable 3' blocks, for example, as described in International Publication No. WO 04/018497, U.S. Patent Application Publication No. 2007/0166705A1, and U.S. Pat. No. 7,057,026, each of which is incorporated herein by reference. For example, repeated cycles of SBS reagents can be delivered to a flow cell having target nucleic acids attached thereto, for example, as a result of the bridge amplification protocol. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, Mass., USA, part number M55055), by exposure to heat or alkali, cleavage of ribonucleotides incorporated into amplification products otherwise comprised of deoxyribonucleotides, photochemical cleavage or cleavage of a peptide linker. After the linearization operation a sequencing primer can be delivered to the flow cell under conditions for hybridization of the sequencing primer to the target nucleic acids that are to be sequenced.

A flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'-OH group available to direct further sequence extension and therefore the polymerase cannot add further nucleotides. The SBS extension reagent can be removed and replaced with scan reagent containing components that protect the sample under excitation with radiation. Example components for scan reagent are described in U.S. Patent Application Publication No. 2008/0280773 A1 and U.S. patent application Ser. No. 13/018,255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Example deblock reagents that are useful for respective blocking groups are described in WO004018497, US 2007/0166705A1 and U.S. Pat. No. 7,057,026, each of which is incorporated herein by reference. The deblock reagent can be washed away leaving target nucleic acids hybridized to extended primers having 3'-OH groups that are now competent for addition of a further nucleotide. Accordingly the cycles of adding extension reagent, scan reagent, and deblock reagent, with optional washes between one or more of the operations, can be repeated until a desired sequence is obtained. The above cycles can be carried out using a single extension reagent delivery operation per cycle when each of the modified nucleotides has a different label attached thereto, known to correspond to the particular base. The different labels facilitate discrimination between the nucleotides added during each incorporation operation. Alternatively, each cycle can include separate operations of extension reagent delivery followed by separate operations of scan reagent delivery and detection, in which case two or more of the nucleotides can have the same label and can be distinguished based on the known order of delivery.

Although the sequencing operation has been discussed above with respect to a particular SBS protocol, it will be understood that other protocols for sequencing any of a variety of other molecular analyses can be carried out as desired.

Then, the one or more processors of the system receive the sequencing data for subsequent analysis. The sequencing data may be formatted in various manners, such as in a .BAM file. The sequencing data may include, for example, a number of sample reads. The sequencing data may include a plurality of sample reads that have corresponding sample sequences of the nucleotides. Although only one sample read is discussed, it should be understood that the sequencing data may include, for example, hundreds, thousands, hundreds of thousands, or millions of sample reads. Different sample reads may have different numbers of nucleotides. For example, a sample read may range between 10 nucleotides to about 500 nucleotides or more. The sample reads may span the entire genome of the source(s). As one example, the sample reads are directed toward predetermined genetic loci, such as those genetic loci having suspected STRs or suspected SNPs.

Each sample read may include a sequence of nucleotides, which may be referred to as a sample sequence, sample fragment or a target sequence. The sample sequence may include, for example, primer sequences, flanking sequences, and a target sequence. The number of nucleotides within the sample sequence may include 30, 40, 50, 60, 70, 80, 90, 100 or more. In some implementations, one or more the sample reads (or sample sequences) includes at least 150 nucleotides, 200 nucleotides, 300 nucleotides, 400 nucleotides, 500 nucleotides, or more. In some implementations, the sample reads may include more than 1000 nucleotides, 2000 nucleotides, or more. The sample reads (or the sample sequences) may include primer sequences at one or both ends.

Next, the one or more processors analyze the sequencing data to obtain potential variant call(s) and a sample variant frequency of the sample variant call(s). The operation may also be referred to as a variant call application or variant caller. Thus, the variant caller identifies or detects variants and the variant classifier classifies the detected variants as somatic or germline. Alternative variant callers may be utilized in accordance with implementations herein, wherein different variant callers may be used based on the type of sequencing operation being performed, based on features of the sample that are of interest and the like. One non-limiting example of a variant call application, such as the Pisces™ application by Illumina Inc. (San Diego, CA) hosted at github.com/Illumina/Pisces and described in the article Dunn, Tamsen & Berry, Gwenn & Emig-Agius, Dorothea & Jiang, Yu & Iyer, Anita & Udar, Nitin & Strömberg, Michael. (2017). Pisces: An Accurate and Versatile Single Sample Somatic and Germline Variant Caller. 595-595. 10.1145/3107411.3108203, the complete subject matter of which is expressly incorporated herein by reference in its entirety.

Such a variant call application can comprise four sequentially executed modules:

(1) Pisces Read Stitcher: Reduces noise by stitching paired reads in a BAM (read one and read two of the same molecule) into consensus reads. The output is a stitched BAM.

(2) Pisces Variant Caller: Calls small SNVs, insertions and deletions. Pisces includes a variant-collapsing algorithm to coalesce variants broken up by read boundaries, basic filtering algorithms, and a simple Poisson-based variant confidence-scoring algorithm. The output is a VCF.

(3) Pisces Variant Quality Recalibrator (VQR): In the event that the variant calls overwhelmingly follow a pattern associated with thermal damage or FFPE deamination, the VQR step will downgrade the variant Q score of the suspect variant calls. The output is an adjusted VCF.

(4) Pisces Variant Phaser (Scylla): Uses a read-backed greedy clustering method to assemble small variants into complex alleles from clonal subpopulations. This allows for the more accurate determination of functional consequence by downstream tools. The output is an adjusted VCF.

Additionally or alternatively, the operation may utilize the variant call application Strelka™ application by Illumina Inc. hosted at https://github.com/Illumina/strelka and described in the article T Saunders, Christopher & Wong, Wendy & Swamy, Sajani & Becq, Jennifer & J Murray, Lisa & Cheetham, Keira. (2012). Strelka: Accurate somatic small-variant calling from sequenced tumor-normal sample pairs. Bioinformatics (Oxford, England). 28. 1811-7. 10.1093/bioinformatics/bts271, the complete subject matter of which is expressly incorporated herein by reference in its entirety. Furthermore, additionally or alternatively, the operation may utilize the variant call application Strelka2™ application by Illumina Inc. hosted at github.com/Illumina/strelka and described in the article Kim, S., Scheffler, K., Halpern, A. L., Bekritsky, M. A., Noh, E., Kallberg, M., Chen, X., Beyter, D., Krusche, P., and Saunders, C. T. (2017). Strelka2: Fast and accurate variant calling for clinical sequencing applications, the complete subject matter of which is expressly incorporated herein by reference in its entirety. Moreover, additionally or alternatively, the operation may utilize a variant annotation/call tool, such as the Nirvana™ application by Illumina Inc. hosted at github.com/Illumina/Nirvana/wiki and described in the article Stromberg, Michael & Roy, Rajat & Lajugie, Julien & Jiang, Yu & Li, Haochen & Margulies, Elliott. (2017). Nirvana: Clinical Grade Variant Annotator. 596-596. 10.1145/3107411.3108204, the complete subject matter of which is expressly incorporated herein by reference in its entirety.

Such a variant annotation/call tool can apply different algorithmic techniques such as those disclosed in Nirvana:

a. Identifying all overlapping transcripts with Interval Array: For functional annotation, we can identify all transcripts overlapping a variant and an interval tree can be used. However, since a set of intervals can be static, we were able to further optimize it to an Interval Array. An interval tree returns all overlapping transcripts in $O(\min(n, k \lg n))$ time, where n is the number of intervals in the tree and k is the number of overlapping intervals. In practice, since k is really small compared to n for most variants, the effective runtime on interval tree would be $O(k \lg n)$. We improved to $O(\lg n+k)$ by creating an interval array where all intervals are stored in a sorted array so that we only need to find the first overlapping interval and then enumerate through the remaining (k−1).

b. CNVs/SVs (Yu): annotations for Copy Number Variation and Structural Variants can be provided. Similar to the annotation of small variants, transcripts overlapping with the SV and also previously reported structural variants can be annotated in online databases. Unlike the small variants, not all overlapping transcripts need be annotated, since too many transcripts will be overlapped with a large SVs. Instead, all overlapping transcripts can be annotated that belong to a partial overlapping gene. Specifically, for these transcripts, the impacted introns, exons and the consequences caused by the structural variants can be reported. An option to allow output all overlapping transcripts is available, but the basic information for these transcripts can be reported, such as gene symbol, flag whether it is canonical overlap or partial overlapped with the transcripts. For each SV/CNV, it is also of interest to know if these variants have been studied and their frequencies in different populations. Hence, we reported overlapping SVs in external databases, such as 1000 genomes, DGV and ClinGen. To avoid using an arbitrary cutoff to determine which SV is overlapped, instead all overlapping transcripts can be used and the reciprocal overlap can be calculated, i.e. the overlapping length divided by the minimum of the length of these two SVs.

c. Reporting supplementary annotations: Supplementary annotations are of two types: small and structural variants (SVs). SVs can be modeled as intervals and use the interval array discussed above to identify overlapping SVs. Small variants are modeled as points and matched by position and (optionally) allele. As such, they are searched using a binary-search-like algorithm. Since the supplementary annotation database can be quite large, a much smaller index is created to map chromosome positions to file locations where the supplementary annotation resides. The index is a sorted array of objects (made up of chromosome position and file location) that can be binary searched using position. To keep the index size small, multiple positions (up to a certain max count) are compressed to one object that stores the values for the first position and only deltas for subsequent positions. Since we use Binary search, the runtime is O(lg n), where n is the number of items in the database.
d. VEP cache files
e. Transcript Database: The Transcript Cache (cache) and Supplementary database (SAdb) files are serialized dump of data objects such as transcripts and supplementary annotations. We use Ensembl VEP cache as our data source for cache. To create the cache, all transcripts are inserted in an interval array and the final state of the array is stored in the cache files. Thus, during annotation, we only need to load a pre-computed interval array and perform searches on it. Since the cache is loaded up in memory and searching is very fast (described above), finding overlapping transcripts is extremely quick in Nirvana (profiled to less than 1% of total runtime?).
f. Supplementary Database: The data sources for SAdb are listed under supplementary material. The SAdb for small variants is produced by a k-way merge of all data sources such that each object in the database (identified by reference name and position) holds all relevant supplementary annotations. Issues encountered during parsing data source files have been documented in detail in Nirvana's home page. To limit memory usage, only the SA index is loaded up in memory. This index allows a quick lookup of the file location for a supplementary annotation. However, since the data has to be fetched from disk, adding supplementary annotation has been identified as Nirvana's largest bottleneck (profiled at ~30% of total runtime.)
g. Consequence and Sequence Ontology: Nirvana's functional annotation (when provided) follows the Sequence Ontology (SO)(sequenceontology.org/) guidelines. On occasions, we had the opportunity to identify issues in the current SO and collaborate with the SO team to improve the state of annotation.

Such a variant annotation tool can include pre-processing. For example, Nirvana included a large number of annotations from External data sources, like ExAC, EVS, 1000 Genomes project, dbSNP, ClinVar, Cosmic, DGV and ClinGen. To make full use of these databases, we have to sanitize the information from them. We implemented different strategy to deal with different conflicts that exist from different data sources. For example, in case of multiple dbSNP entries for the same position and alternate allele, we join all ids into a comma separated list of ids; if there are multiple entries with different CAF values for the same allele, we use the first CAF value. For conflicting ExAC and EVS entries, we consider the number of sample counts and the entry with higher sample count is used. In 1000 Genome Projects, we removed the allele frequency of the conflicting allele. Another issue is inaccurate information. We mainly extracted the allele frequencies information from 1000 Genome Projects, however, we noticed that for GRCh38, the allele frequency reported in the info field did not exclude samples with genotype not available, leading to deflated frequencies for variants which are not available for all samples. To guarantee the accuracy of our annotation, we use all of the individual level genotype to compute the true allele frequencies. As we know, the same variants can have different representations based on different alignments. To make sure we can accurately report the information for already identified variants, we have to preprocess the variants from different resources to make them have consistent representation. For all external data sources, we trimmed alleles to remove duplicated nucleotides in both reference allele and alternative allele. For ClinVar, we directly parsed the xml file we performed a five-prime alignment for all variants, which is often used in vcf file. Different databases can contain the same set of information. To avoid unnecessary duplicates, we removed some duplicated information. For example, we removed variants in DGV which has data source as 1000 genome projects, since we already reported these variants in 1000 genomes with more detailed information.

In accordance with at least some implementations, the variant call application provides calls for low frequency variants, germline calling and the like. As non-limiting example, the variant call application may run on tumor-only samples and/or tumor-normal paired samples. The variant call application may search for single nucleotide variations (SNV), multiple nucleotide variations (MNV), indels and the like. The variant call application identifies variants, while filtering for mismatches due to sequencing or sample preparation errors. For each variant, the variant caller identifies the reference sequence, a position of the variant, and the potential variant sequence(s) (e.g., A to C SNV, or AG to A deletion). The variant call application identifies the sample sequence (or sample fragment), a reference sequence/fragment, and a variant call as an indication that a variant is present. The variant call application may identify raw fragments, and output a designation of the raw fragments, a count of the number of raw fragments that verify the potential variant call, the position within the raw fragment at which a supporting variant occurred and other relevant information. Non-limiting examples of raw fragments include a duplex stitched fragment, a simplex stitched fragment, a duplex un-stitched fragment and a simplex un-stitched fragment.

The variant call application may output the calls in various formats, such as in a .VCF or .GVCF file. By way of example only, the variant call application may be included in a MiSeqReporter pipeline (e.g., when implemented on the MiSeq® sequencer instrument). Optionally, the application may be implemented with various workflows. The analysis may include a single protocol or a combination of protocols that analyze the sample reads in a designated manner to obtain desired information.

Then, the one or more processors perform a validation operation in connection with the potential variant call. The validation operation may be based on a quality score, and/or a hierarchy of tiered tests, as explained hereafter. When the validation operation authenticates or verifies that the potential variant call, the validation operation passes the variant call information (from the variant call application) to the sample report generator. Alternatively, when the validation operation invalidates or disqualifies the potential variant call, the validation operation passes a corresponding indication (e.g., a negative indicator, a no call indicator, an in-valid call indicator) to the sample report generator. The validation operation also may pass a confidence score related to a degree of confidence that the variant call is correct or the in-valid call designation is correct.

Next, the one or more processors generate and store a sample report. The sample report may include, for example, information regarding a plurality of genetic loci with respect to the sample. For example, for each genetic locus of a predetermined set of genetic loci, the sample report may at least one of provide a genotype call; indicate that a genotype call cannot be made; provide a confidence score on a certainty of the genotype call; or indicate potential problems with an assay regarding one or more genetic loci. The sample report may also indicate a gender of an individual that provided a sample and/or indicate that the sample include multiple sources. As used herein, a "sample report" may include digital data (e.g., a data file) of a genetic locus or predetermined set of genetic locus and/or a printed report of the genetic locus or the set of genetic loci. Thus, generating or providing may include creating a data file and/or printing the sample report, or displaying the sample report.

The sample report may indicate that a variant call was determined, but was not validated. When a variant call is determined invalid, the sample report may indicate additional information regarding the basis for the determination to not validate the variant call. For example, the additional information in the report may include a description of the raw fragments and an extent (e.g., a count) to which the raw fragments support or contradicted the variant call. Additionally or alternatively, the additional information in the report may include the quality score obtained in accordance with implementations described herein.

Variant Call Application

Implementations disclosed herein include analyzing sequencing data to identify potential variant calls. Variant calling may be performed upon stored data for a previously performed sequencing operation. Additionally or alternatively, it may be performed in real time while a sequencing operation is being performed. Each of the sample reads is assigned to corresponding genetic loci. The sample reads may be assigned to corresponding genetic loci based on the sequence of the nucleotides of the sample read or, in other words, the order of nucleotides within the sample read (e.g., A, C, G, T). Based on this analysis, the sample read may be designated as including a possible variant/allele of a particular genetic locus. The sample read may be collected (or aggregated or binned) with other sample reads that have been designated as including possible variants/alleles of the genetic locus. The assigning operation may also be referred to as a calling operation in which the sample read is identified as being possibly associated with a particular genetic position/locus. The sample reads may be analyzed to locate one or more identifying sequences (e.g., primer sequences) of nucleotides that differentiate the sample read from other sample reads. More specifically, the identifying sequence(s) may identify the sample read from other sample reads as being associated with a particular genetic locus.

The assigning operation may include analyzing the series of n nucleotides of the identifying sequence to determine if the series of n nucleotides of the identifying sequence effectively matches with one or more of the select sequences. In particular implementations, the assigning operation may include analyzing the first n nucleotides of the sample sequence to determine if the first n nucleotides of the sample sequence effectively matches with one or more of the select sequences. The number n may have a variety of values, which may be programmed into the protocol or entered by a user. For example, the number n may be defined as the number of nucleotides of the shortest select sequence within the database. The number n may be a predetermined number. The predetermined number may be, for example, 10, 11, 12, 13, 14, 15, 16, 17, 18, 19, 20, 21, 22, 23, 24, 25, 26, 27, 28, 29, or 30 nucleotides. However, fewer or more nucleotides may be used in other implementations. The number n may also be selected by an individual, such as a user of the system. The number n may be based on one or more conditions. For instance, the number n may be defined as the number of nucleotides of the shortest primer sequence within the database or a designated number, whichever is the smaller number. In some implementations, a minimum value for n may be used, such as 15, such that any primer sequence that is less than 15 nucleotides may be designated as an exception.

In some cases, the series of n nucleotides of an identifying sequence may not precisely match the nucleotides of the select sequence. Nonetheless, the identifying sequence may effectively match the select sequence if the identifying sequence is nearly identical to the select sequence. For example, the sample read may be called for a genetic locus if the series of n nucleotides (e.g., the first n nucleotides) of the identifying sequence match a select sequence with no more than a designated number of mismatches (e.g., 3) and/or a designated number of shifts (e.g., 2). Rules may be established such that each mismatch or shift may count as a difference between the sample read and the primer sequence. If the number of differences is less than a designated number, then the sample read may be called for the corresponding genetic locus (i.e., assigned to the corresponding genetic locus). In some implementations, a matching score may be determined that is based on the number of differences between the identifying sequence of the sample read and the select sequence associated with a genetic locus. If the matching score passes a designated matching threshold, then the genetic locus that corresponds to the select sequence may be designated as a potential locus for the sample read. In some implementations, subsequent analysis may be performed to determine whether the sample read is called for the genetic locus.

If the sample read effectively matches one of the select sequences in the database (i.e., exactly matches or nearly matches as described above), then the sample read is assigned or designated to the genetic locus that correlates to the select sequence. This may be referred to as locus calling or provisional-locus calling, wherein the sample read is called for the genetic locus that correlates to the select sequence. However, as discussed above, a sample read may be called for more than one genetic locus. In such implementations, further analysis may be performed to call or assign the sample read for only one of the potential genetic loci. In some implementations, the sample read that is compared to the database of reference sequences is the first read from paired-end sequencing. When performing paired-end sequencing, a second read (representing a raw fragment) is obtained that correlates to the sample read. After assigning, the subsequent analysis that is performed with the assigned reads may be based on the type of genetic locus that has been called for the assigned read.

Next, the sample reads are analyzed to identify potential variant calls. Among other things, the results of the analysis identify the potential variant call, a sample variant frequency, a reference sequence and a position within the genomic sequence of interest at which the variant occurred. For example, if a genetic locus is known for including SNPs, then the assigned reads that have been called for the genetic locus may undergo analysis to identify the SNPs of the assigned reads. If the genetic locus is known for including polymorphic repetitive DNA elements, then the assigned reads may be analyzed to identify or characterize the polymorphic repetitive DNA elements within the sample reads. In some implementations, if an assigned read effectively matches with an STR locus and an SNP locus, a warning or flag may be assigned to the sample read. The sample read may be designated as both an STR locus and an SNP locus. The analyzing may include aligning the assigned reads in accordance with an alignment protocol to determine sequences and/or lengths of the assigned reads. The alignment protocol may include the method described in International Patent Application No. PCT/US2013/030867 (Publication No. WO 2014/142831), filed on Mar. 15, 2013, which is herein incorporated by reference in its entirety.

Then, the one or more processors analyze raw fragments to determine whether supporting variants exist at corresponding positions within the raw fragments. Various types of raw fragments may be identified. For example, the variant caller may identify a type of raw fragment that exhibits a variant that validates the original variant call. For example, the type of raw fragment may represent a duplex stitched fragment, a simplex stitched fragment, a duplex un-stitched fragment or a simplex un-stitched fragment. Optionally other raw fragments may be identified instead of or in addition to the foregoing examples. In connection with identifying each type of raw fragment, the variant caller also identifies the position, within the raw fragment, at which the supporting variant occurred, as well as a count of the number of raw fragments that exhibited the supporting variant. For example, the variant caller may output an indication that 10 reads of raw fragments were identified to represent duplex stitched fragments having a supporting variant at a particular position X. The variant caller may also output indication that five reads of raw fragments were identified to represent simplex un-stitched fragments having a supporting variant at a particular position Y. The variant caller may also output a number of raw fragments that corresponded to reference sequences and thus did not include a supporting variant that would otherwise provide evidence validating the potential variant call at the genomic sequence of interest.

Next, a count is maintained of the raw fragments that include supporting variants, as well as the position at which the supporting variant occurred. Additionally or alternatively, a count may be maintained of the raw fragments that did not include supporting variants at the position of interest (relative to the position of the potential variant call in the sample read or sample fragment). Additionally or alternatively, a count may be maintained of raw fragments that correspond to a reference sequence and do not authenticate or confirm the potential variant call. The information determined is output to the variant call validation application, including a count and type of the raw fragments that support the potential variant call, positions of the supporting variance in the raw fragments, a count of the raw fragments that do not support the potential variant call and the like.

When a potential variant call is identified, the process outputs an indicating of the potential variant call, the variant sequence, the variant position and a reference sequence associated therewith. The variant call is designated to represent a "potential" variant as errors may cause the call process to identify a false variant. In accordance with implementations herein, the potential variant call is analyzed to reduce and eliminate false variants or false positives. Additionally or alternatively, the process analyzes one or more raw fragments associated with a sample read and outputs a corresponding variant call associated with the raw fragments.

Variant Filter

Variant filter 111 includes a convolutional neural network (CNN) and a fully-connected neural network (FCNN). The input to the variant filter 111 are overlaid samples of nucleotide sequences from the overlaid samples database 119. The nucleotide sequences from the nucleotide sequences database 169 are overlaid with repeat patterns from the repeat patterns database 196 to generate overlaid samples. An overlayer 181 overlays repeat patterns on nucleotide sequences from the database 169 to produce overlaid samples that are stored in the overlaid samples database 119. The simulator 116 feeds combinations of repeat patterns overlaid on at least 100 nucleotide sequences in at least 100 overlaid samples to the variant filter for analysis. When overlaid samples with repeat pattern under test are given as input the variant filter 111, the variant filter 111 outputs classification scores for likelihood that the variant nucleotide in each of the overlaid samples is a true variant or a false variant. Finally, the analyzer 194 causes display of the classification scores as a distribution for each of the repeat factors to support evaluation of sequence-specific error causation by the repeat patterns.

Repeat Patterns

A repeat pattern generator 171 generates repeat patterns "rp" using homopolymer or copolymer patterns of length "n" with distinct repeat factors "m". The homopolymer repeat patterns comprise a single base (A, C, G, or T) while copolymer repeat patterns comprise more than one bases. A "repeat pattern" is generated by applying a "repeat factor (m)" to a "pattern". The relationship between a pattern of length (n), a repeat factor (m) and a repeat pattern (rp) is represented by equation (1) as:

$$\text{pattern} * m = rp \tag{1}$$

Table 1, presents examples of homopolymer repeat patterns. The length of homopolymer patterns is one i.e., "n=1".

| n = Pattern Length | Pattern | m = Repeat Factor | Repeat Pattern (rp) |
|---|---|---|---|
| 1 | A | 5 | AAAAA (5 As) |
| 1 | A | 9 | AAAAAAAAA (9 As) |
| 1 | A | 13 | AAAAAAAAAAAAA (13 As) |
| 1 | A | 17 | AAAAAAAAAAAAAAAAA (17 As) |
| 1 | A | 21 | AAAAAAAAAAAAAAAAAAAAA (21 As) |
| 1 | A | 25 | AAAAAAAAAAAAAAAAAAAAAAAAA (25 As) |
| 1 | C | 5 | CCCCC (5 Cs) |
| 1 | C | 9 | CCCCCCCCC (9 Cs) |
| 1 | C | 13 | CCCCCCCCCCCCC (13 Cs) |
| 1 | C | 17 | CCCCCCCCCCCCCCCCC (17 Cs) |
| 1 | C | 21 | CCCCCCCCCCCCCCCCCCCCC (21 Cs) |
| 1 | C | 25 | CCCCCCCCCCCCCCCCCCCCCCCCC (25 Cs) |
| 1 | T | 5 | TTTTT (5 Cs) |
| 1 | T | 9 | TTTTTTTTT (9 Ts) |
| 1 | T | 13 | TTTTTTTTTTTTT (13 Ts) |
| 1 | T | 17 | TTTTTTTTTTTTTTTTT (17 Ts) |
| 1 | T | 21 | TTTTTTTTTTTTTTTTTTTTT (21 Ts) |
| 1 | T | 25 | TTTTTTTTTTTTTTTTTTTTTTTTT (25 Ts) |
| 1 | G | 5 | TTTTT (5 Cs) |
| 1 | G | 9 | TTTTTTTTT (9 Ts) |
| 1 | G | 13 | TTTTTTTTTTTTT (13 Ts) |
| 1 | G | 17 | TTTTTTTTTTTTTTTTT (17 Ts) |

| n = Pattern Length | m = Repeat Pattern | Repeat Factor | Repeat Pattern (rp) |
|---|---|---|---|
| 1 | G | 21 | TTTTTTTTTTTTTTTTTTTTT (21 Ts) |
| 1 | G | 25 | TTTTTTTTTTTTTTTTTTTTTTTTT (25 Ts) |

A table 2, presents example repeat patterns of copolymers. The length of copolymer patterns is greater than one i.e., "n>1".

| n = Pattern Length | m = Repeat Pattern | Repeat Factor | Repeat Pattern (rp) |
|---|---|---|---|
| 2 | AC | 1 | AC (1 AC) |
| 2 | AC | 3 | ACACAC (3 ACs) |
| 2 | AC | 5 | ACACACACAC (5 ACs) |
| 2 | AC | 7 | ACACACACACACAC (7 ACs) |
| 2 | AC | 9 | ACACACACACACACACAC (9 ACs) |
| 2 | AC | 11 | ACACACACACACACACACACAC (11 ACs) |
| 2 | TA | 1 | TA (1 TA) |
| 2 | TA | 3 | TATATA (3 TAs) |
| 2 | TA | 5 | TATATATATA (5 TAs) |
| 2 | TA | 7 | TATATATATATATA (7 TAs) |
| 2 | TA | 9 | TATATATATATATATATA (9 TAs) |
| 2 | TA | 11 | TATATATATATATATATATATA (11 TAs) |
| 3 | AAT | 1 | AAT (1 AAT) |
| 3 | AAT | 2 | AATAAT (2 AATs) |
| 3 | AAT | 3 | AATAATAAT (3 AATs) |
| 3 | AAT | 4 | AATAATAATAAT (4 AATs) |
| 3 | AAT | 5 | AATAATAATAATAAT (5 AATs) |
| 3 | AAT | 6 | AATAATAATAATAATAAT (6 AATs) |
| 4 | CTAT | 1 | CTAT (1 CTAT) |
| 4 | CTAT | 2 | CTATCTAT (2 CTATs) |
| 4 | CTAT | 3 | CTATCTATCTAT (3 CTATs) |
| 4 | CTAT | 4 | CTATCTATCTATCTAT (4 CTATs) |
| 4 | CTAT | 5 | CTATCTATCTATCTATCTAT (5 CTATs) |
| 4 | CTAT | 6 | CTATCTATCTATCTATCTATCTAT (5 CTATs) |

Variant Filter

Figure 2:
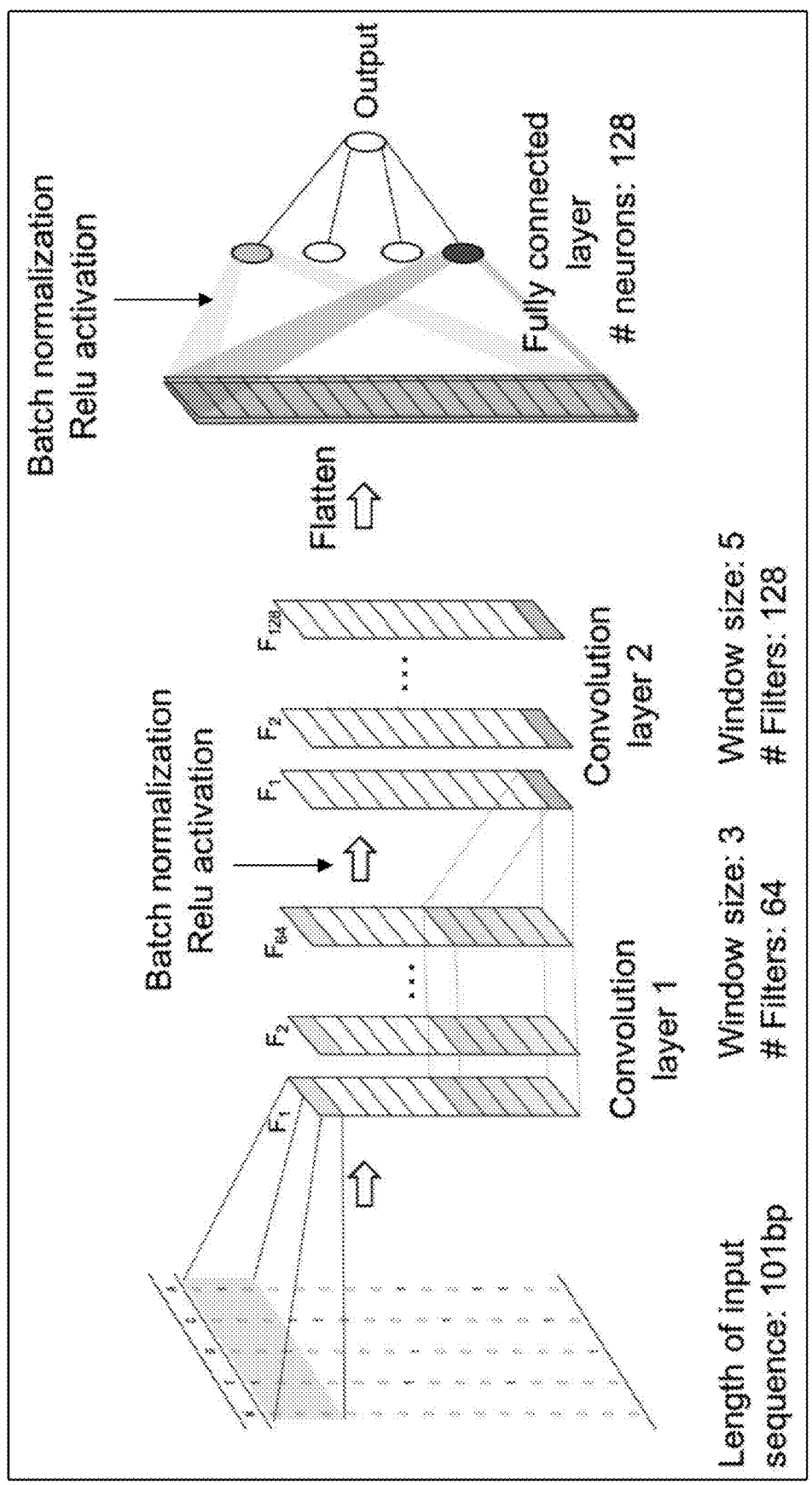
FIG. 2 illustrates an example architecture of the variant filter. The variant filter has a hierarchical structure built on a convolutional neural network (CNN) and a fully-connected neural network (FCNN). DeepPOLY uses the variant filter to test known sequence patterns for their effect on variant filtering.

FIG. 2 illustrates an example architecture 200 of the variant filter 111. The variant filter 111 has a hierarchical structure built on a convolutional neural network (CNN) and a fully-connected neural network (FCNN). DeepPOLY uses the variant filter 111 to test known sequence patterns for their effect on variant filtering. The input to variant filter 111 comprises nucleotide sequences of length 101 having a variant nucleotide at the center and flanked on the left and the right by 50 nucleotides. It is understood that nucleotide sequences of different lengths can be used as inputs to the variant filter 111.

The convolutional neural network comprises convolution layers which perform the convolution operation between the input values and convolution filters (matrix of weights) that are learned over many gradient update iterations during the training.

Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m x n) is called the receptive field. A same convolution filter is applied across different positions of the input, which reduces the number of weights learned. It also allows location invariant learning, i.e., if an important pattern exists in the input, the convolution filters learn it no matter where it is in the sequence. Additional details about convolutional neural network can be found in I. J. Goodfellow, D. Warde-Farley, M. Mirza, A. Courville, and Y. Bengio, "CONVOLUTIONAL NETWORKS," Deep Learning, MIT Press, 2016; J. Wu, "INTRODUCTION TO CONVOLUTIONAL NEURAL NETWORKS," Nanjing University, 2017; and N. ten DIJKE, "Convolutional Neural Networks for Regulatory Genomics," Master's Thesis, Universiteit Leiden Opleiding Informatica, 17 Jun. 2017, the complete subject matter of which is expressly incorporated herein by reference in its entirety. The convolutional neural network architecture illustrated in FIG. 2 has two convolution layers. The first convolution layer processes the input using 64 filters of size 3 each. The output of the first convolution layer is passed through a batch normalization layer.

Distribution of each layer of the convolutional neural network changes during training and it varies from one layer to another. This reduces the convergence speed of the optimization algorithm. Batch normalization (Ioffe and Szegedy 2015) is a technique to overcome this problem. Denoting the input of a batch normalization layer with x and its output using z, batch normalization applies the following transformation on x:

$$z = \frac{x - \mu}{\sqrt{\sigma^2 + \varepsilon}} \gamma + \beta$$

Batch normalization applies mean-variance normalization on the input x using $\mu$ and $\sigma$ and linearly scales and shifts it using $\gamma$ and $\beta$. The normalization parameters $\mu$ and $\sigma$ are computed for the current layer over the training set using a method called exponential moving average. In other words, they are not trainable parameters. In contrast, $\gamma$ and $\beta$ are trainable parameters. The values for $\mu$ and $\sigma$ calculated above during training are used in forward pass during production. A rectified linear unit (ReLU) nonlinearity function is applied to the output of batch normalization layer to produce a normalized output. Other examples of nonlinearity functions include sigmoid, hyperbolic tangent (tanh), and leaky ReLU.

A second convolution layer operates 128 filters of size 5 on the normalized output. The example CNN shown in FIG. 2, includes a flattening layer which flattens the output from the second convolution layer to a one dimensional array which is passed through a second set of batch normalization and ReLU activations layers. The normalized output from the second convolution layer is fed to the fully-connected neural network (FCNN). The fully-connected neural network comprises fully-connected layers—each neuron receives input from all the previous layer's neurons and sends its output to every neuron in the next layer. This contrasts with how convolutional layers work where the neurons send their output to only some of the neurons in the next layer. The neurons of the fully-connected layers are optimized over many gradient update iterations during the training. Additional details about the fully-connected neural network can be found in I. J. Goodfellow, D. Warde-Farley, M. Mirza, A. Courville, and Y. Bengio, "CONVOLUTIONAL NETWORKS," Deep Learning, MIT Press, 2016; J. Wu, "INTRODUCTION TO CONVOLUTIONAL NEURAL NETWORKS," Nanjing University, 2017; and N. ten DIJKE, "Convolutional Neural Networks for Regulatory Genomics," Master's Thesis, Universiteit Leiden Opleiding Informatica, 17 Jun. 2017, the complete subject matter of which is expressly incorporated herein by reference in its entirety. A classification layer (e.g., softmax layer) following the full-connected layers produces classification scores for likelihood that each candidate variant at the target nucleotide position is a true variant or a false variant. The classification layer can be a softmax layer or a sigmoid layer. The number of classes and their type can be modified, depending on the implementation.

Figure 3:
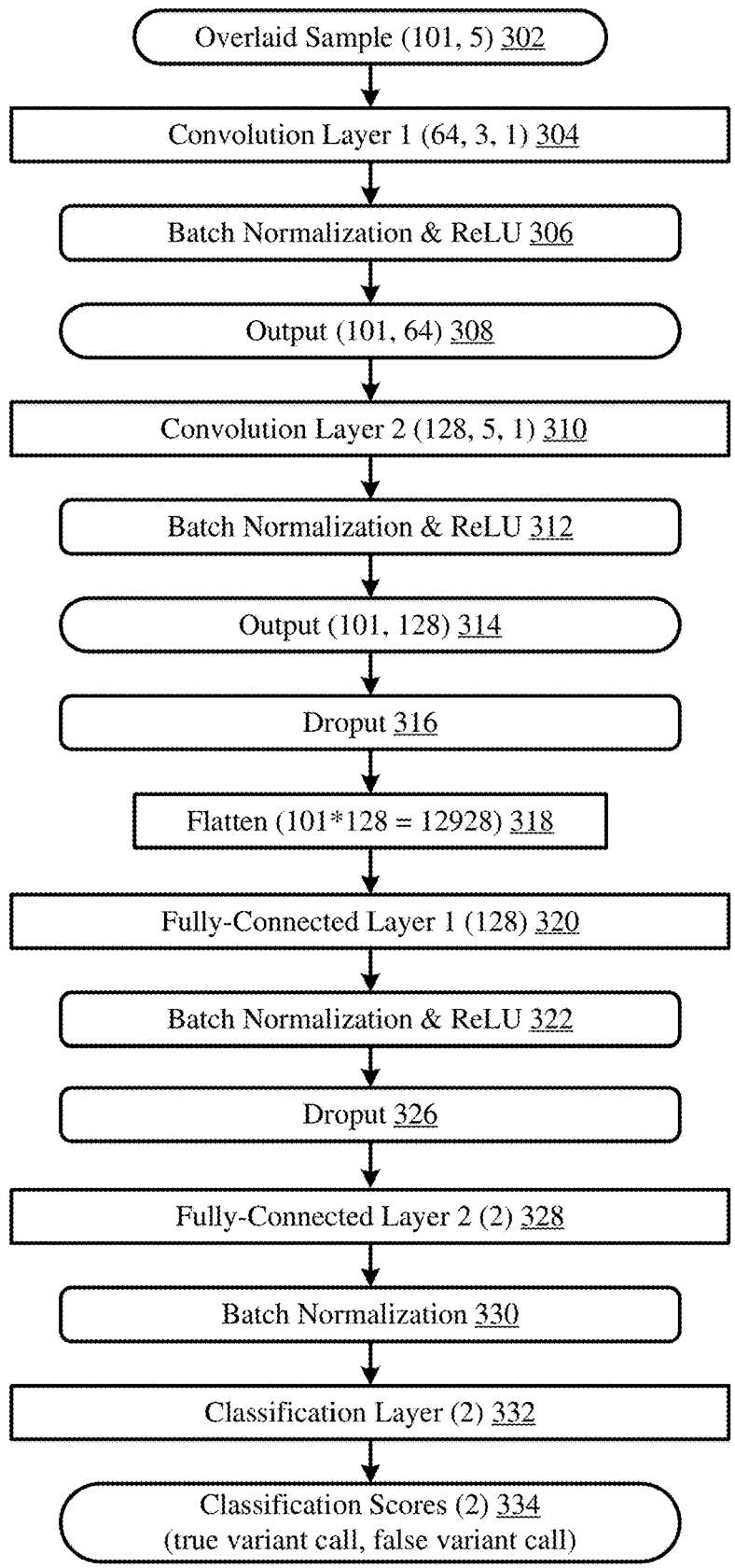
FIG. 3 shows one implementation of the processing pipeline of the variant filter.

FIG. 3 shows one implementation of the processing pipeline 300 of the variant filter 111. In the illustrated implementation, the convolution neural network (CNN) has two convolution layers and the fully-connected neural network (FCNN) has two fully-connected layers. In other implementations, the variant filter 111, and its convolution neural network and fully-connected neural network, can have additional, fewer, or different parameters and hyperparameters. Some examples of parameters are number of convolution layers, number of batch normalization and ReLU layers, number of fully-connected layers, number of convolution filters in respective convolution layers, number of neurons in respective fully-connected layers, number of outputs produced by the final classification layer, and residual connectivity. Some examples of hyperparameters are window size of the convolution filters, stride length of the convolution filters, padding, and dilation. In the discussion below, the term "layer" refers to an algorithm implemented in code as a software logic or module. Some examples of layers can be found in Keras™ documentation available at keras.io/layers/about-keras-layers/, the complete subject matter of which is expressly incorporated herein by reference in its entirety.

A one-hot encoded input sequence 302 is fed to a first convolution layer 304 of the convolutional neural network (CNN). The dimensionality of the input sequence 302 is 101, 5, where 101 represents the 101 nucleotides in the input sequence 302 with a particular variant at a center target position flanked by 50 nucleotides on each side, and 5 represents the 5 channels A, T, C, G, N used to encode the input sequence 302. The preparation of input sequences 302 is described with reference to FIG. 5.

The first convolution layer 304 has 64 filters, each of which convolves over the input sequence 302 with a window size of 3 and stride length of 1. The convolution is followed by batch normalization and ReLU nonlinearity layers 306. What results is an output (feature map) 308 of dimensionality 101, 64. Output 308 can be regarded as the first intermediate convolved feature.

Output 308 is fed as input to a second convolution layer 310 of the convolutional neural network. The second convolution layer 310 has 128 filters, each of which convolves over the output 308 with a window size of 5 and stride length of 1. The convolution is followed by batch normalization and ReLU nonlinearity layers 312. What results is an output (feature map) 314 of dimensionality 101, 128. Output 314 can be regarded as the second intermediate convolved feature and also the final output of the convolutional neural network.

Dropout is an effective technique to prevent a neural network from overfitting. It works by randomly dropping a fraction of neurons from the network in each iteration of the training. This means that output and gradients of selected neurons are set to zero so they do not have any impact on forward and backward passes. In FIG. 3, dropout is performed at dropout layer 316 using a probability of 0.5.

After processing the output through the dropout layer, the output is flattened by a flattening layer 318 to allow downstream processing by the fully-connected neural network. Flattening includes vectorizing the output 314 to have either one row or one column. That is, by way of example, converting the output 314 of dimensionality 101, 128 into a flattened vector of dimensionality 1, 12928 (1 row and 101×128=12928 columns).

The flattened output of dimensionality 1, 12928 from flattening layer 318 is then fed as input to the fully-connected neural network (FCNN). The fully-connected neural network has two fully-connected layers 320 and 328. The first fully-connected layer 320 has 128 neurons, which are fully connected to 2 neurons in the second fully-connected layer 328. The first fully-connected layer 320 is followed by a batch normalization, ReLU non-linearity and dropout layers 322, and 326. The second fully-connected layer 328 is followed by a batch normalization layer 330. The classification layer 332 (e.g., softmax) has 2 neurons which output the 2 classification scores or probabilities 334 for the particular variant being a true variant or a false variant.

Performance of the Variant Caller on Held-Out Data

Figure 4A:
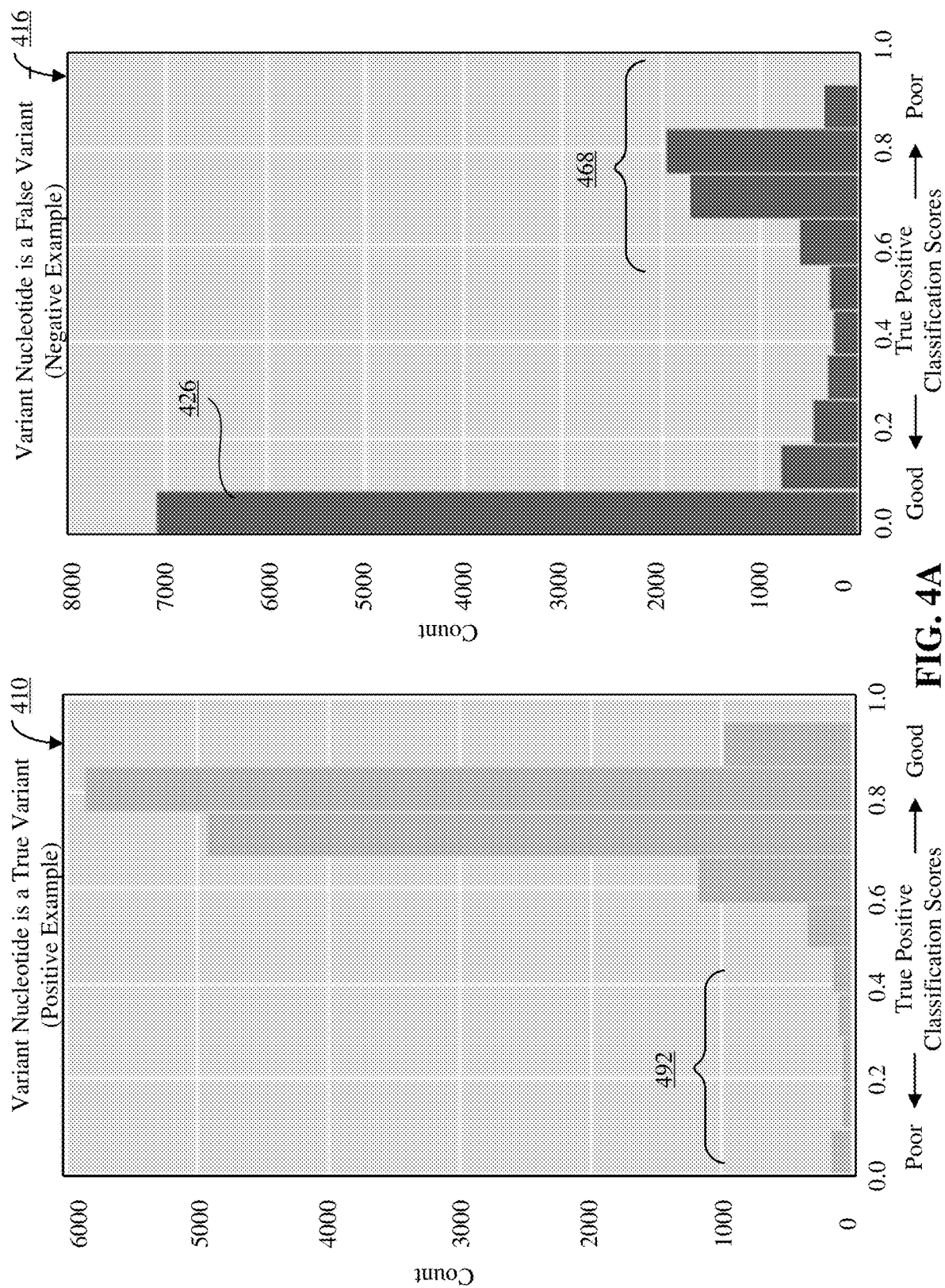
FIG. 4A shows true and false positive plots that graphically illustrate the variant filter's performance on held-out data.

FIG. 4A shows true and false positive plots that graphically illustrate the variant filter's performance on held-out data. There are 28,000 validation examples in the held-out data set, with about 14,000 validation examples of true variants (positive examples) and 14,000 validation examples of false variants (negative examples). The two plots 410 and 416 show performance of the variant filter 111 when 28,000 validation examples are fed as input during the validation stage. The graphs 410 and 416 plot the classification scores along x-axis indicating the confidence of the trained model in predicting the true variants and the false variants as true positive. Thus, the trained model is expected to produce high classification scores for the true variants and low classification scores for the false variants. The height of the vertical bars indicate the count of validation examples with respective classification scores along the x-axis.

Plot 416 shows that the variant filter 111 classified more than 7,000 validation examples of false variants as "low confidence true positives" (i.e., classification score <0.5 (e.g., 426)), confirming that the model successfully learned to classify negative examples as false variants. The variant filter 111 classified some validation examples of false variants as "high confidence true positives" (e.g., 468). This occurred because, in the training data and/or in the held-out data, some de novo variants observed in only one child were mislabeled as false variants when they were actually true variants.

Plot 410 shows that the variant filter 111 classified more than 11,000 validation examples of true variants as "high confidence true positives" (i.e., classification score >0.5), confirming that the model successfully learned to classify positive examples as true variants.

Figure 4B:
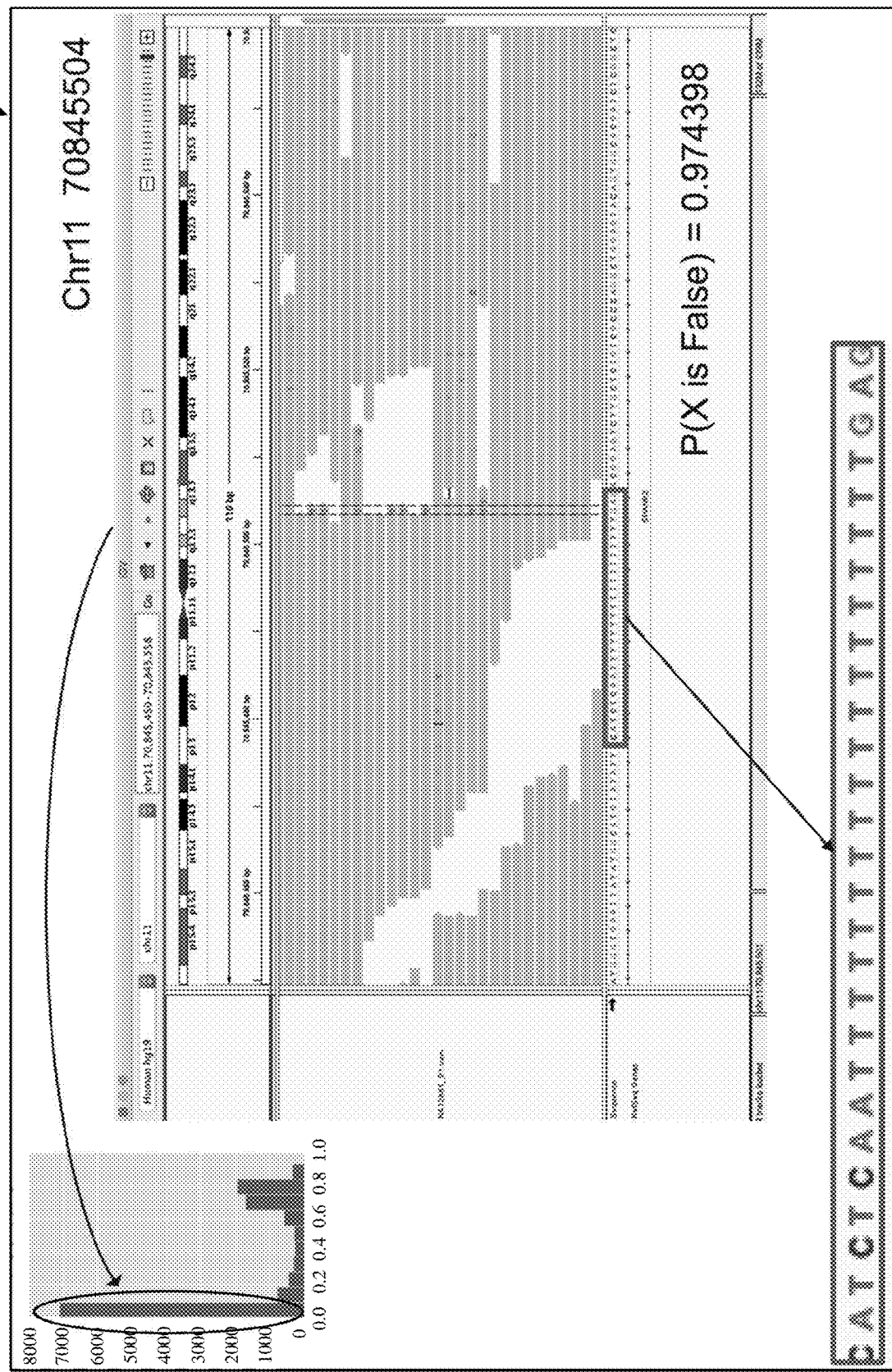
FIGS. 4B and 4C show pile-up images of aligned reads that validate the variant filter's accuracy.

In FIG. 4B, the classification results of the variant filter 111 are compared against analysis derived from a pile-up image that aligns reads produced by a sequencer to a reference sequence 498. The reference sequence 498 comprises a homopolymer repeat pattern of length 18 of a single base "T" as shown by label 494 in FIG. 4B. The pile-up image shows that at least seven reads (indicated by reference label 455) reported a "T" base at the position of a "G" nucleotide with respect to the reference genome 498. Therefore, there are two possible resulting calls for calling the base at this position in the sequence: "G" or "T". The ground truth from the "platinum genomes pedigree" shows that none of the parents and grandparents have a variant nucleotide at this position in their respective reference sequences. Therefore, "T" base call is determined as "false positive" that occurred due to a sequencing error. In addition, the pile-up image shows that the "Ts" appear only at the end of read 1, which further confirms that the variant is false.

The performance of the variant filter 111 is consistent with the above analysis because the variant filter 111 classified the nucleotide at this position as a false variant with a high confidence, as illustrated in FIG. 4B by "P(X is False)=0.974398".

Figure 4C:
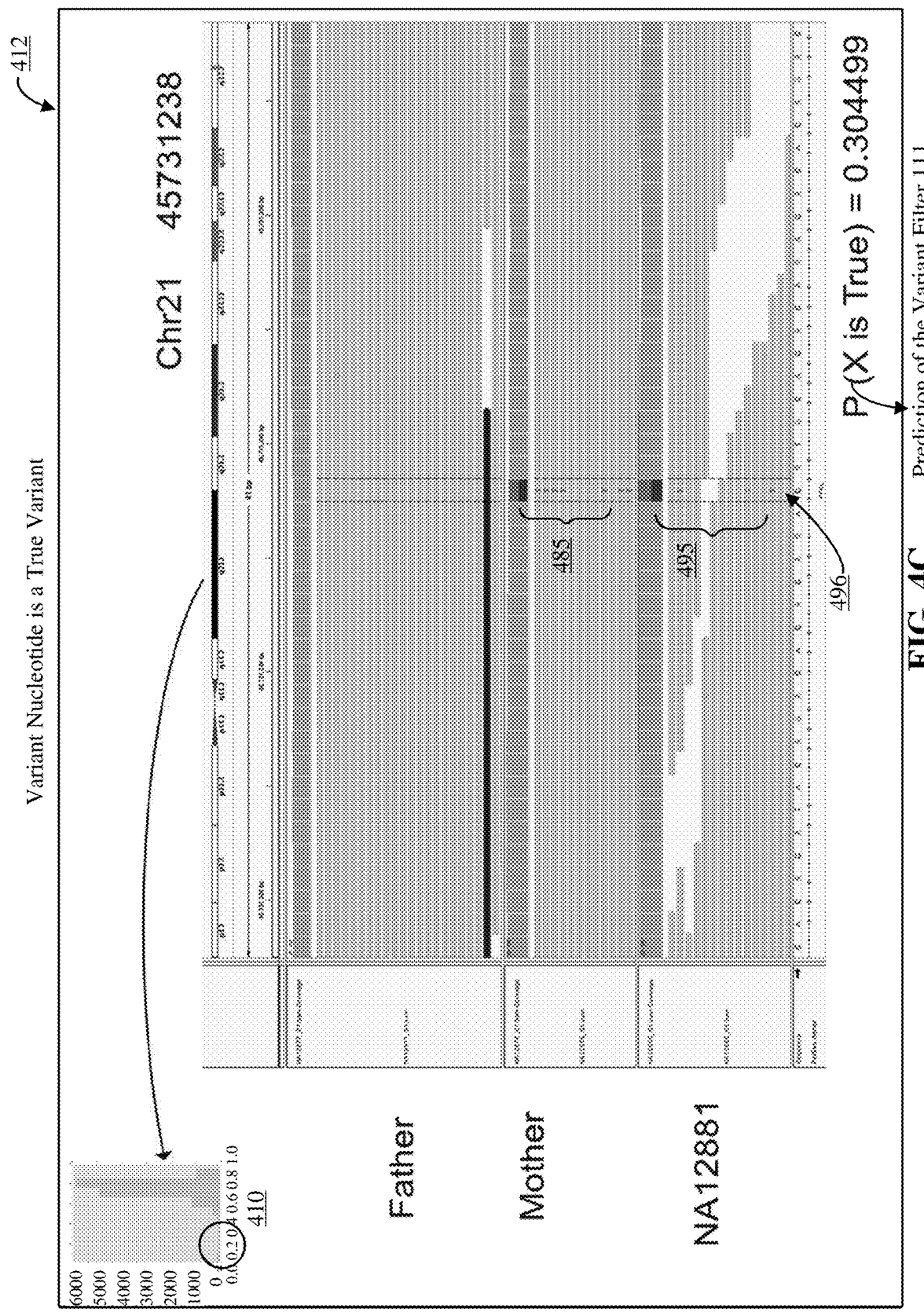

FIG. 4C shows pile-up image 412 of sequencing reads for an example that contains a true variant. The sequencing reads for the child (labelled as "NA12881") has at least three "T" nucleotides identified by a label 495. The reference sequence has a "C" nucleotide at that position as identified by a label 496. However, the mother's sequencing reads indicate at least seven "T" nucleotides at the same position. Therefore, this is an instance of an example having a true variant as shown by the plot 410 on the top left corner. The variant filter 111 classified this example as a true positive with a low confidence score ("P(X is True)=0.304499"). That is, the variant filter 111 classified the target nucleotide as a false variant (or weakly classified as a true variant) because of presence of a repeat pattern of copolymer "AC" before the target nucleotide's position. The trained sequence considers repeat pattern as a potential sequence-specific error (SSE) and therefore, classified the variant "T" with a low confidence score.

Figure 5:
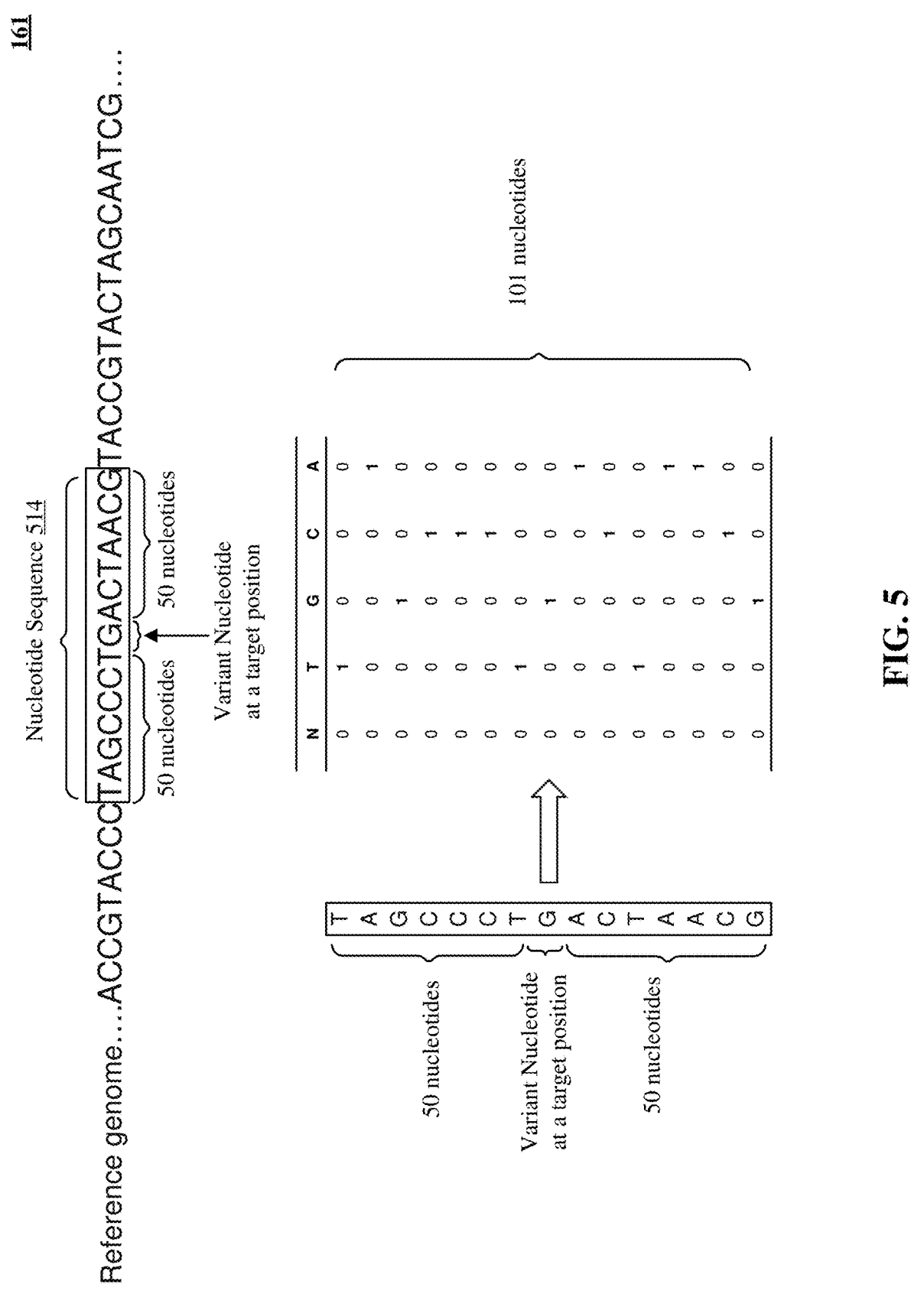

FIG. 5 shows an example input preparation by the input preparer 161 using one-hot encoding to encode the overlaid nucleotide sequences having a variant nucleotide at a target position for input to the variant filter 111. A nucleotide sequence 514 comprising of at least 50 nucleotides on both sides (left and right) of a variant nucleotide at a target position is used for preparing the input. Note that the nucleotide sequence 514 is a portion of the reference genome. In one-hot encoding, each base pair in a sequence is encoded with a binary vector of four bits, with one of the bits being hot (i.e., 1) while other being 0. For instance, T=(1, 0, 0, 0), G=(0, 1, 0, 0), C=(0, 0, 1, 0), and A=(0, 0, 0, 1). In some implementations, an unknown nucleotide is encoded as N=(0, 0, 0, 0). The figure shows an example nucleotide sequence of 101 nucleotides represented using one-hot encoded.

Figure 6:
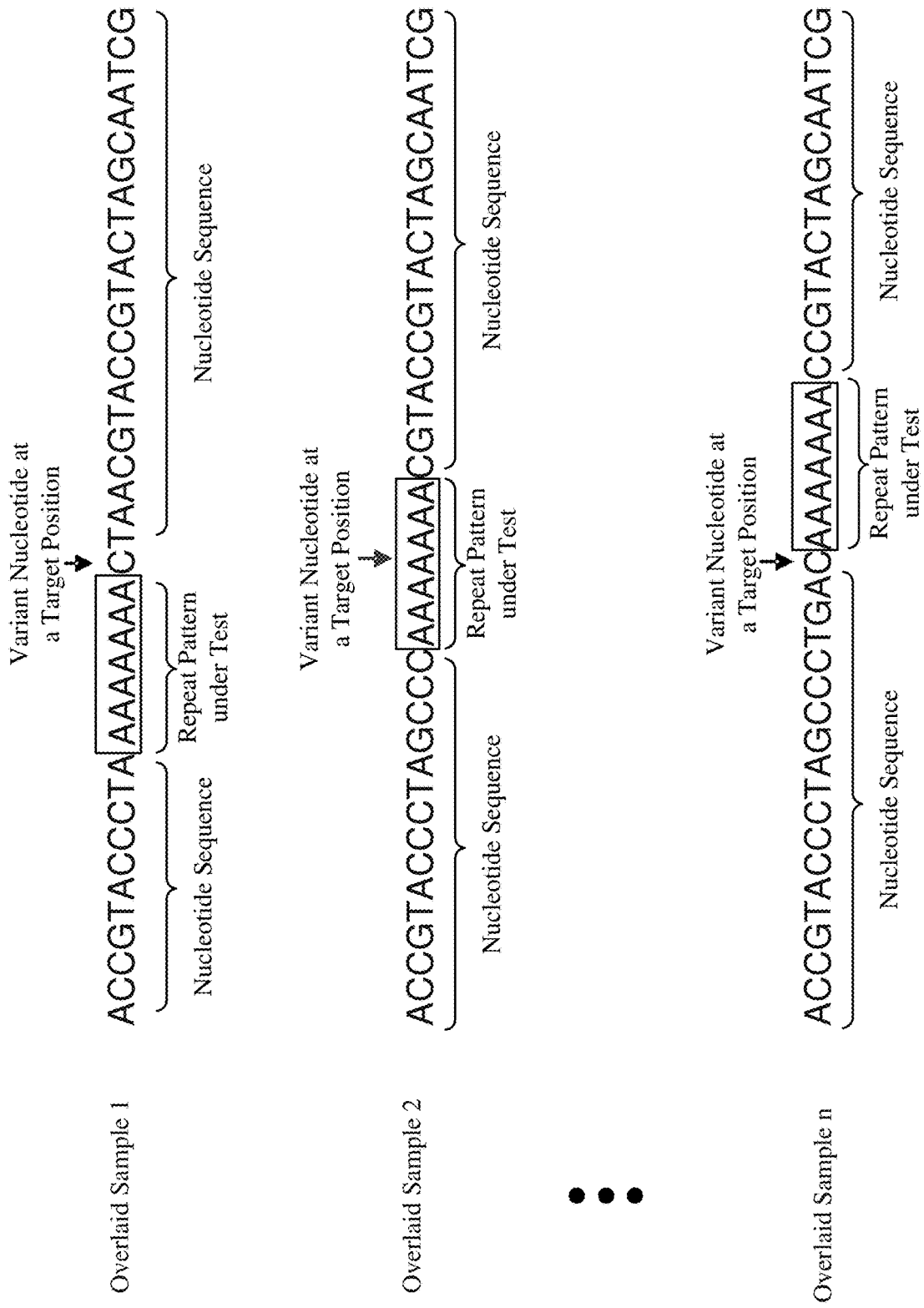
FIG. 6 illustrates examples of overlaid samples produced by the input preparer by overlaying the repeat patterns on nucleotide sequences.

FIG. 6 illustrates preparation of overlaid samples produced by the input preparer by overlaying the repeat patterns on nucleotide sequences. The overlaid samples are stored in the overlaid samples database 119. The example shows an overlaid sample 1 which is generated by overlaying a homopolymer repeat pattern of 7 "A"s to left of a center nucleotide at a target position in overlaid sample. An overlaid sample 2 is created by overlaying the same repeat pattern of 7 "A"s on the nucleotide sequence to include a center nucleotide. A third overlaid sample n is generated by overlaying the repeat pattern of 7 "A"s to the right of a center nucleotide in the overlaid samples.

Figure 7A:
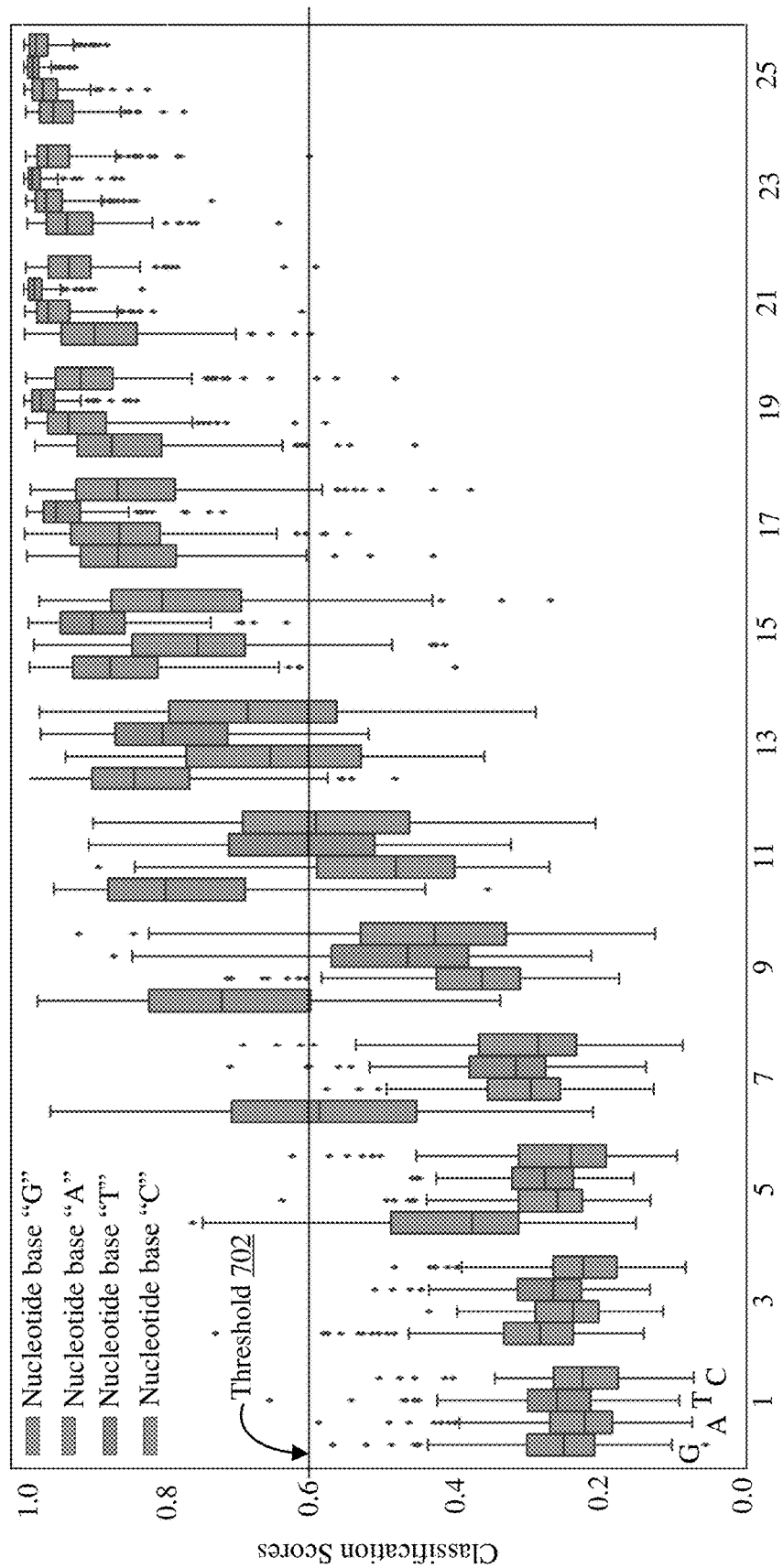
FIG. 7A uses a box-and-whisker plot to identify sequence-specific errors causation by repeat patterns to left of the variant nucleotide at the target position in the overlaid samples.
Figure 7B:
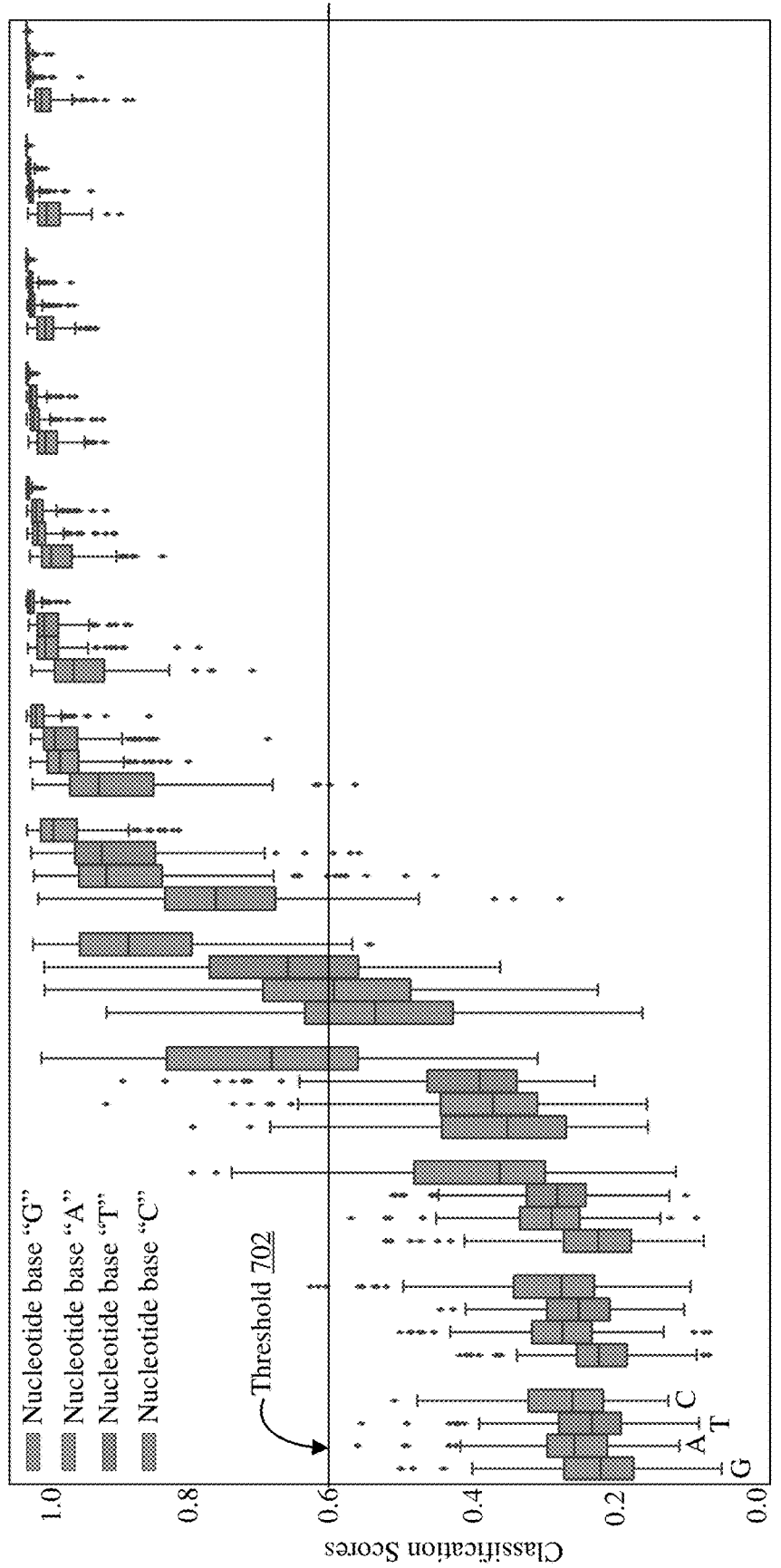
FIG. 7B uses a box-and-whisker plot to identify sequence-specific errors causation by repeat patterns to right of the variant nucleotide at the target position in the overlaid samples.
Figure 7C:
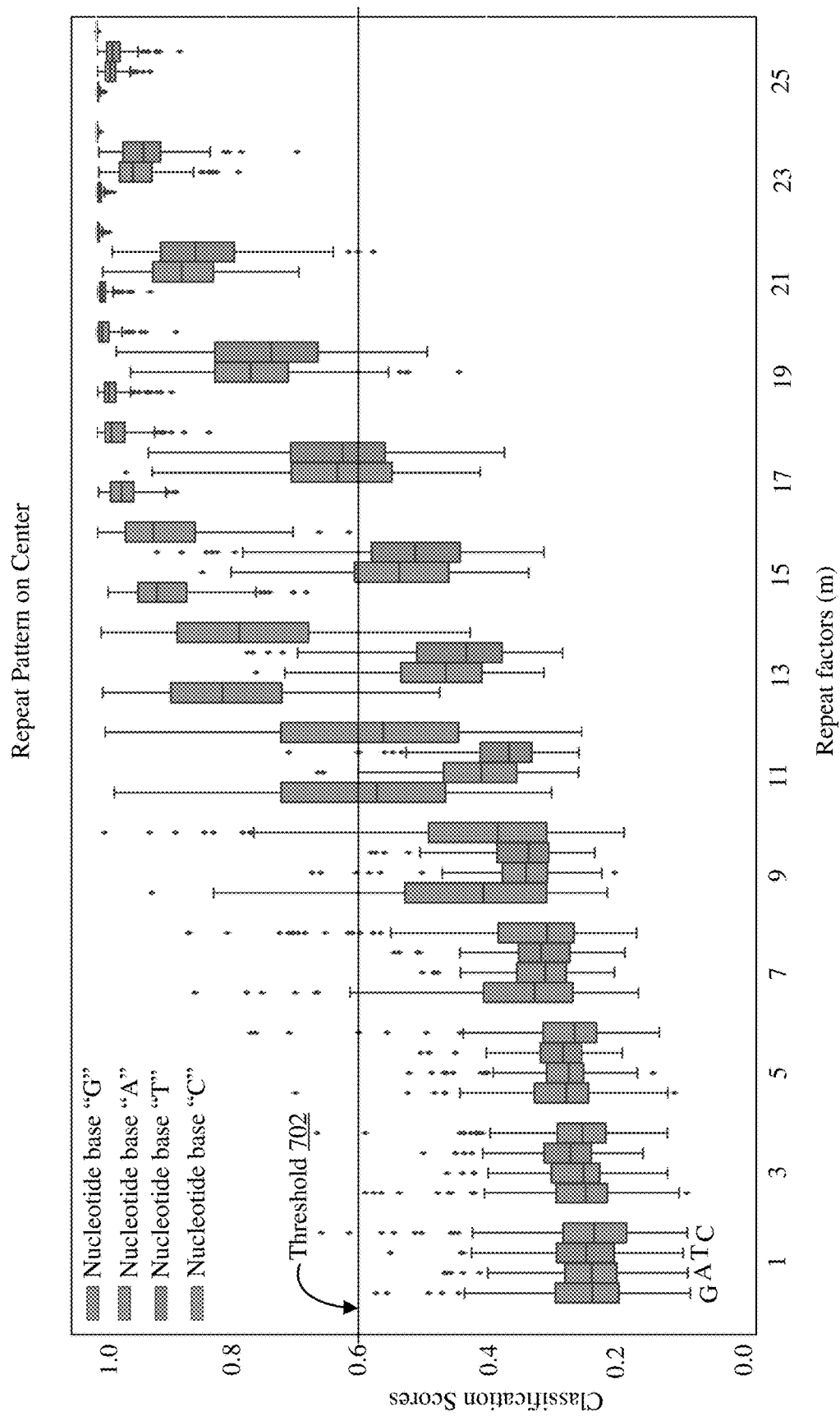
FIG. 7C uses a box-and-whisker plot to identify sequence-specific errors causation by repeat patterns including a variant nucleotide at the target position in the overlaid samples.

The variant filter subsystem, translates analysis by the variant filter 111 into classification scores for likelihood that the variant nucleotide in each of the overlaid samples is a true variant or a false variant. The variant filter subsystem is followed by an analysis subsystem in which the analyzer 194, causes the display of the classification scores as a distribution for each of the repeat factors to support evaluation of sequence-specific error causation by the repeat patterns. FIGS. 7A to 7C present examples of such display from the analyzer 194. FIG. 7A using a box-and-whisker plot to identify sequence-specific error causation by repeat pattern overlaid left of a center nucleotide in the overlaid samples.

The y-axis of the graphical plot shows distribution of the classification scores outputted by the variant filter when the overlaid samples containing different repeat pattern were fed to the variant filter as input. The x-axis shows the repeat factors (m) applied to the pattern that produced the repeat pattern fed as input. The repeat patterns considered here are homopolymers generated by using repeat factors indicated on the x-axis. The example shows four box-and-whisker plots per unique repeat factor value. The four plots correspond to homopolymer repeat patterns of the four type of nucleotides (G, A, T, and C). Each repeat pattern is placed on at least 100 nucleotides sequences to generate 100 overlaid samples fed as input to the CNN of the variant filter 111. In another implementation, at least 200 nucleotide sequences are used to generate at least 200 overlaid samples per repeat pattern. The same process is repeated to generate homopolymer repeat patterns for all repeat factors shown along the x-axis.

The graphical plot in FIG. 7A shows that shorter repeat patterns (length less than 10 nucleotides) of a single base "G" can introduce sequence-specific errors in variant identification. Similarly, shorter repeat patterns of a single base "C" can also introduce some errors while repeat patterns of nucleotides bases "A" and "T" are less likely to cause sequence-specific errors when repeat patterns are short. However, longer repeat patterns (length greater than 10 nucleotides) of all four types of nucleotides cause more sequence specific errors.

FIG. 7B is a box-and-whisker plot displaying classification scores as a distribution for likelihood that a variant nucleotide is true variant or a false variant when repeat patterns are overlaid on a nucleotide sequence to right of a center nucleotide in the overlaid samples. As compared to FIG. 7A, the shorter patterns of homoplymers of a single nucleotide "C" are more likely to cause an error in identification of a true variant. FIG. 7C is a box-and-whisker plot displaying classification scores as a distribution for likelihood that a variant nucleotide is a true variant or a false variant when the repeat patterns include a center nucleotide (at a target position) in the overlaid samples. As compared to FIGS. 7A and 7B, the FIG. 7C shows that shorter repeat patterns of all four nucleotide types are less likely to cause a sequence-specific error in variant identification.

Figure 8A:
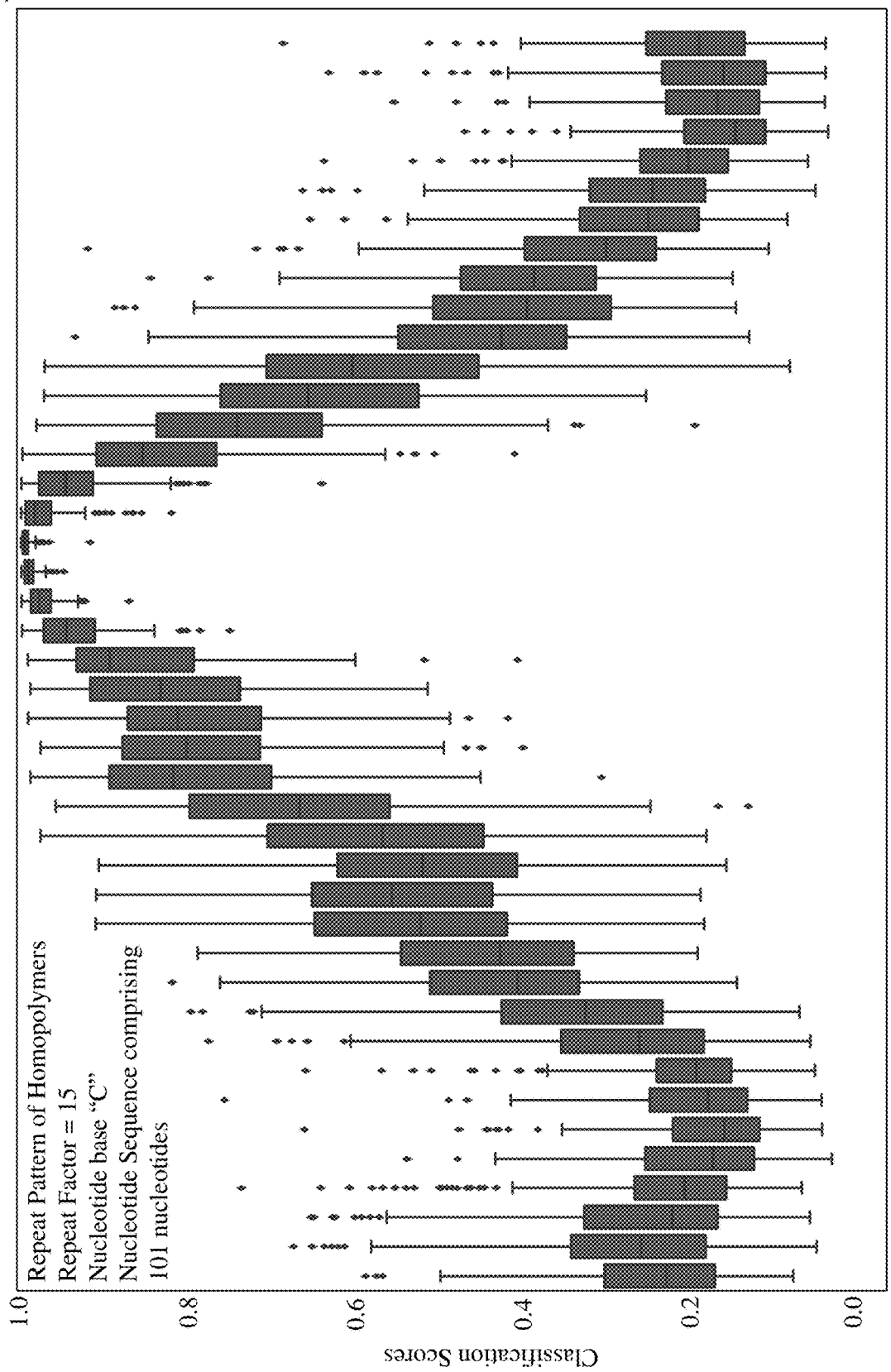
FIG. 8A uses a box-and-whisker plot to identify sequence-specific errors causation by repeat patterns of homopolymers of a single base "C" overlaid at varying offsets on nucleotide sequences.
Figure 8B:
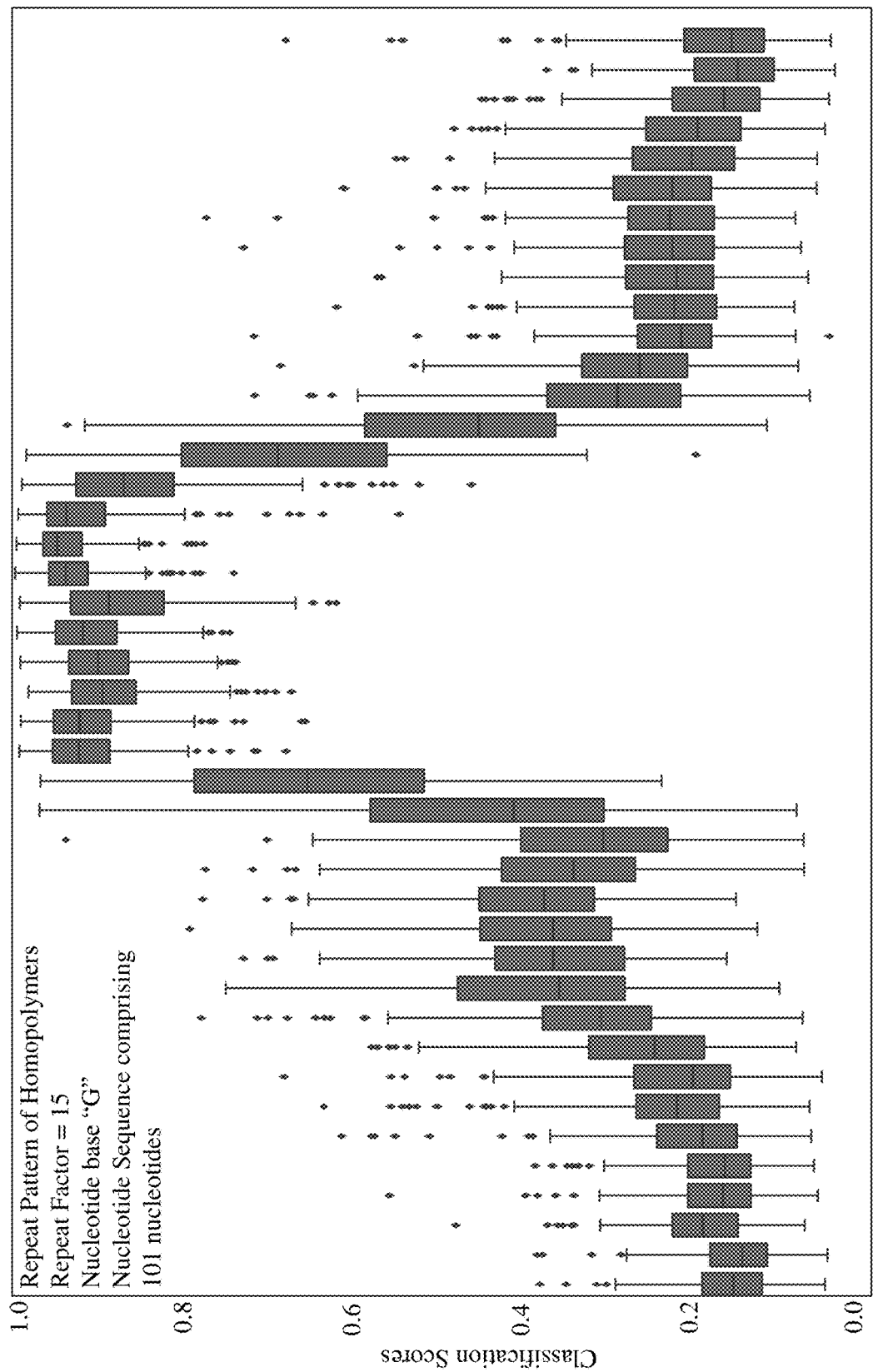
FIG. 8B uses a box-and-whisker plot to identify sequence-specific errors causation by repeat patterns of homopolymers of a single base "G" overlaid at varying offsets on nucleotide sequences.
Figure 8C:
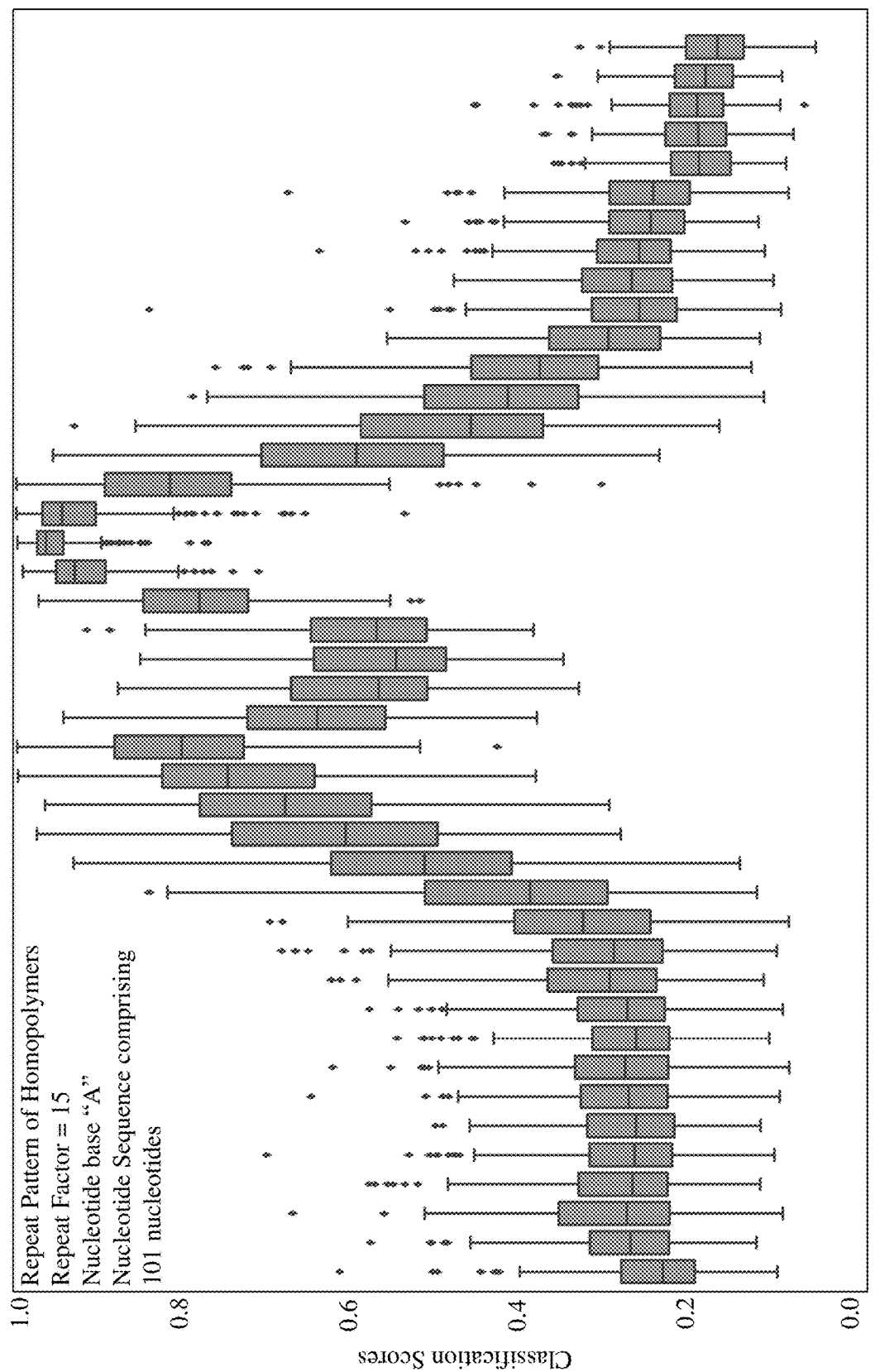
FIG. 8C uses a box-and-whisker plot to identify sequence-specific errors causation by repeat patterns of homopolymers of a single base "A" overlaid at varying offsets on nucleotide sequences.

FIGS. 8A to 8C present graphical plots to identify sequence specific errors causation when the homopolymers repeat patterns of a single base (A, C, G, or T) are overlaid at varying offsets on nucleotide sequences to produce overlaid samples. The varying offsets vary a position at which the repeat patterns are overlaid on the nucleotide sequences. The varying offset is measurable as an offset between an origin position of the repeat patterns and an origin position of the nucleotide sequences. In one implementation, at least ten offsets are used to produce overlaid samples. Ten is a reasonable floor to generate overlaid samples with repeat patterns at a variety of offsets to analyze the sequence specific errors causation.

FIG. 8A is a box-and-whisker plot to identify sequence-specific errors causation by repeat patterns of homopolymers of a single base "C" overlaid at varying offsets on nucleotide sequences. The repeat factor m=15 which means that the repeat pattern is a homopolymer of length 15 of a single base "C". This repeat pattern is overlaid on nucleotide sequences consisting of 101 nucleotides to generate overlaid samples at varying offsets. For each offset value, combinations of repeat patterns overlaid on at least 100 nucleotide sequences in at least 100 overlaid samples are fed to the CNN of the variant filter of FIG. 1. The FIG. 8A shows box-and-whisker plots for offset positions at 0, 2, 4, up to 84 when repeat pattern of 15 single bases "C" is overlaid on the nucleotide sequences. For example, when the offset is "0", the origin position of the repeat pattern coincides with the origin position of the nucleotide sequences. At offset "2", the origin position of the repeat pattern is aligned to the third base (at an index of 2) to overlay the repeat pattern on the nucleotide sequences. As the offset increases, the overlaid repeat pattern is closer to the variant nucleotide at a target position nucleotide sequence. In the example used for the illustration purposes in FIG. 8A, the target nucleotide is at index position of "50" which is the center of the nucleotide sequence comprising 101 nucleotides. As the offset value increases above 50, the repeat pattern moves past the variant nucleotide and is positioned on the right side of the variant nucleotide at the target position.

Figure 8D:
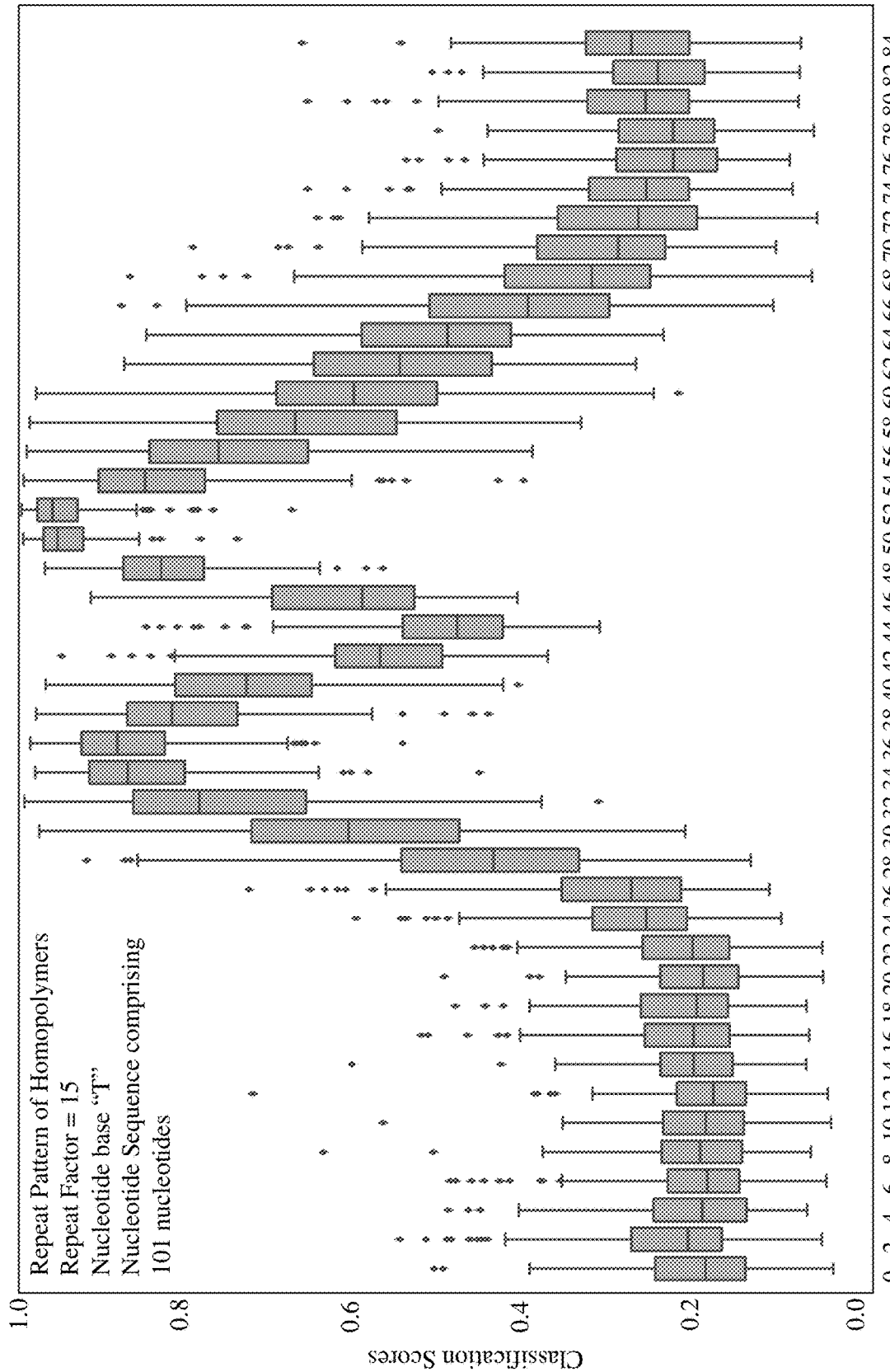
FIG. 8D uses a box-and-whisker plot to identify sequence-specific errors causation by repeat patterns of homopolymers of a single base "T" overlaid at varying offsets on nucleotide sequences.

FIGS. 8B, 8C, and 8D are similar box-and-whisker plots as described above to identify sequence-specific errors causation by repeat patterns of homopolymers of single bases "G", "A", and "T" respectively, overlaid at varying offsets on nucleotide sequences. The repeat factor m=15 for each of the three repeat patterns.

Figure 9:
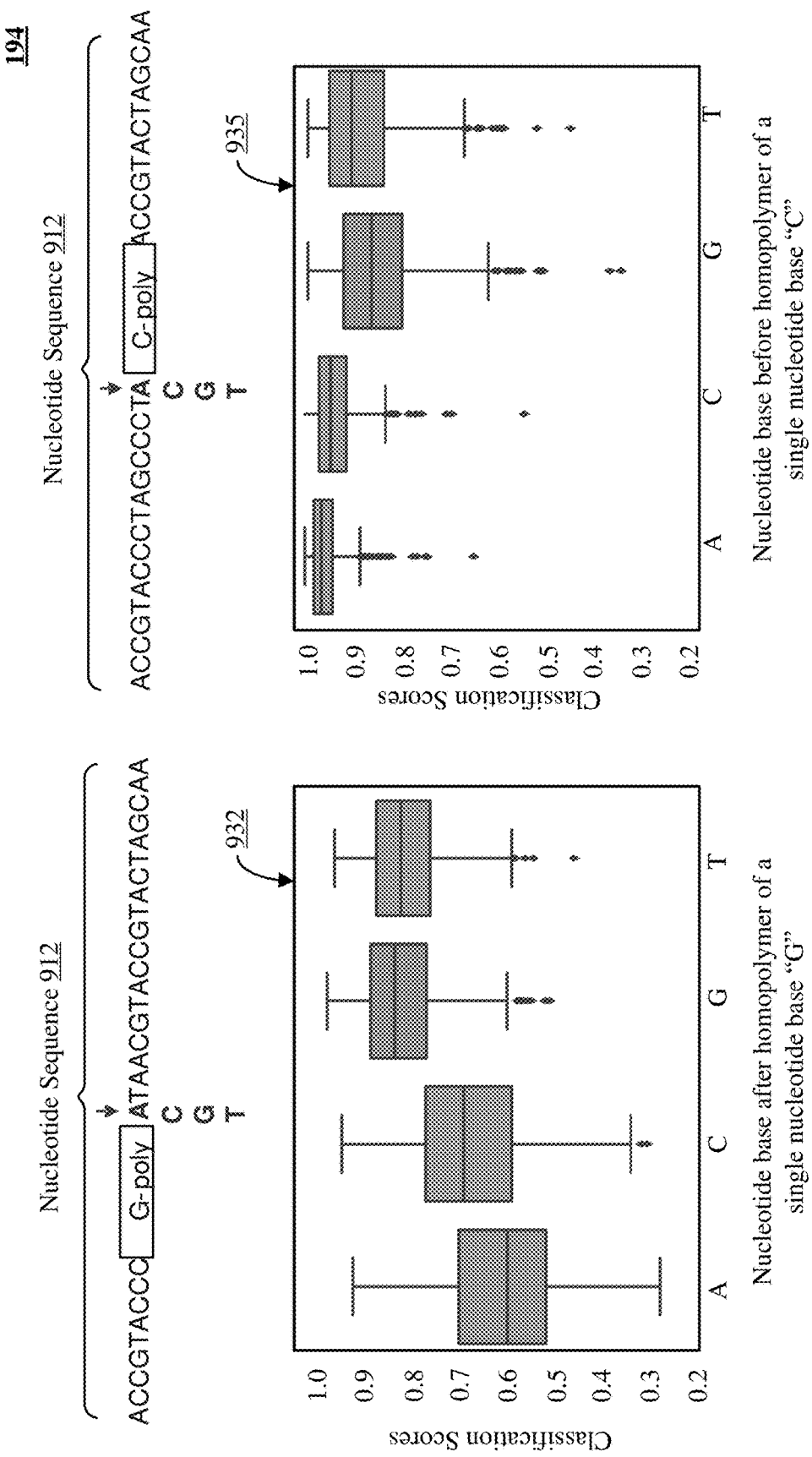
FIG. 9 displays classification scores as a distribution for likelihood that a variant nucleotide is a true variant or a false variant when repeat patterns of homopolymers of a single base are placed one by one "before" and "after" a variant nucleotide of each of the four bases at a target position.

FIG. 9 shows display of classification scores as a distribution for likelihood that a variant nucleotide is a true variant or a false variant when repeat patterns of homopolymers of a single base are overlaid "before" and "after" a variant nucleotide. The homopolymer repeat patterns are overlaid one by one before and after variant nucleotides at a target position to produce overlaid samples. A box-and-whisker plot 932 shows classification scores when a homopolymer repeat pattern of a single base "G" is overlaid to left of a center nucleotide on a nucleotide sequence. The results are generated for four types of nucleotides (A, C, G, and T) as the variant nucleotide at a target position followed by the homopolymer repeat pattern. The results show that classification scores vary by a bigger spread if the target nucleotide is of type "A" and "C".

A graphical plot 935 shows a similar visualization but for a homopolymer repeat pattern of a single base "C" overlaid to right of a center nucleotide on a nucleotide sequence 912. The comparison of box-and-whisker plots show a larger spread of classification scores when a target nucleotide is of type "G".

Figure 10A:
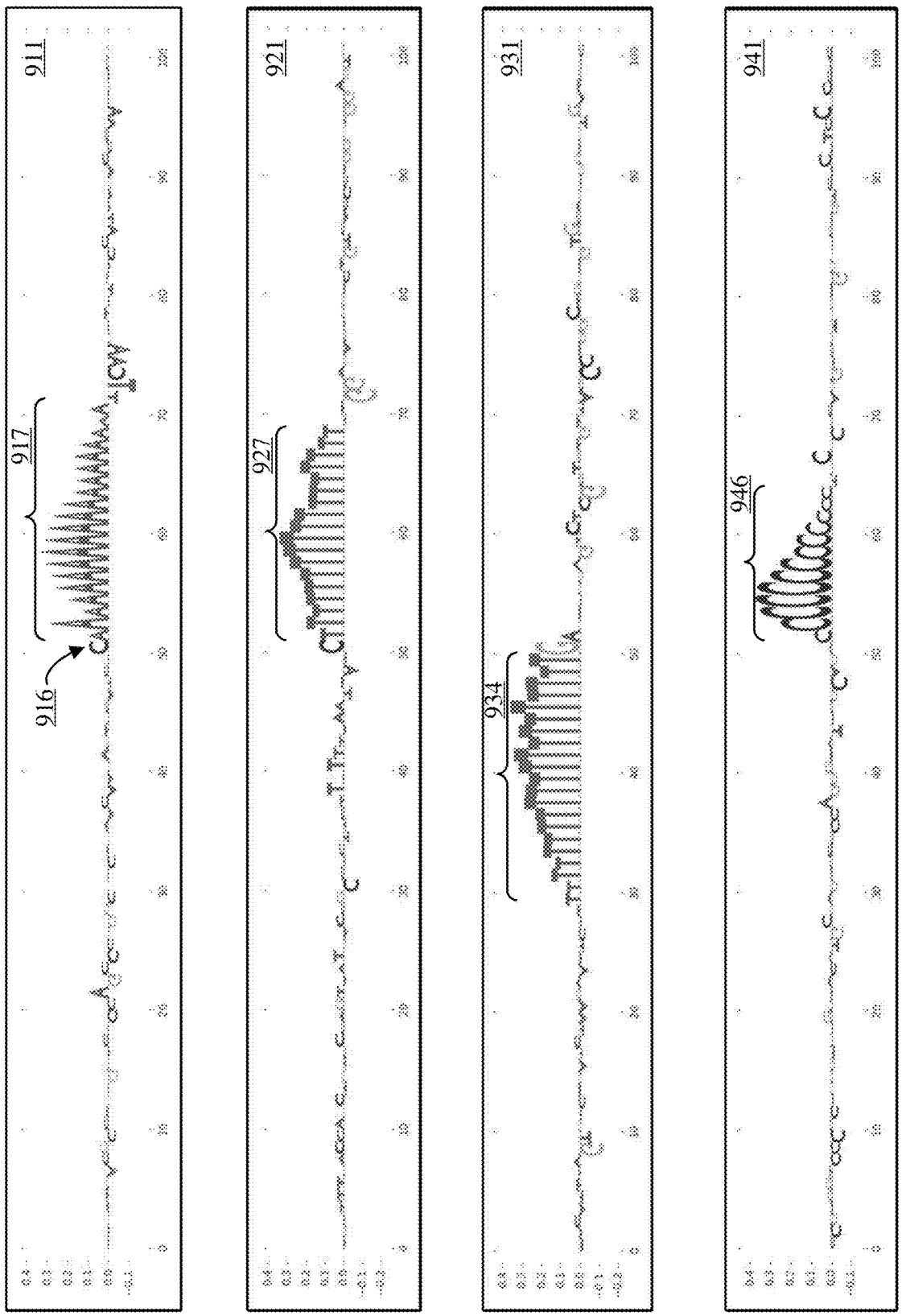
FIGS. 10A to 10C display a representation of naturally occurring repeat patterns of copolymers in each of the sample nucleotide sequences that contribute to a false variant classification.
Figure 10B:
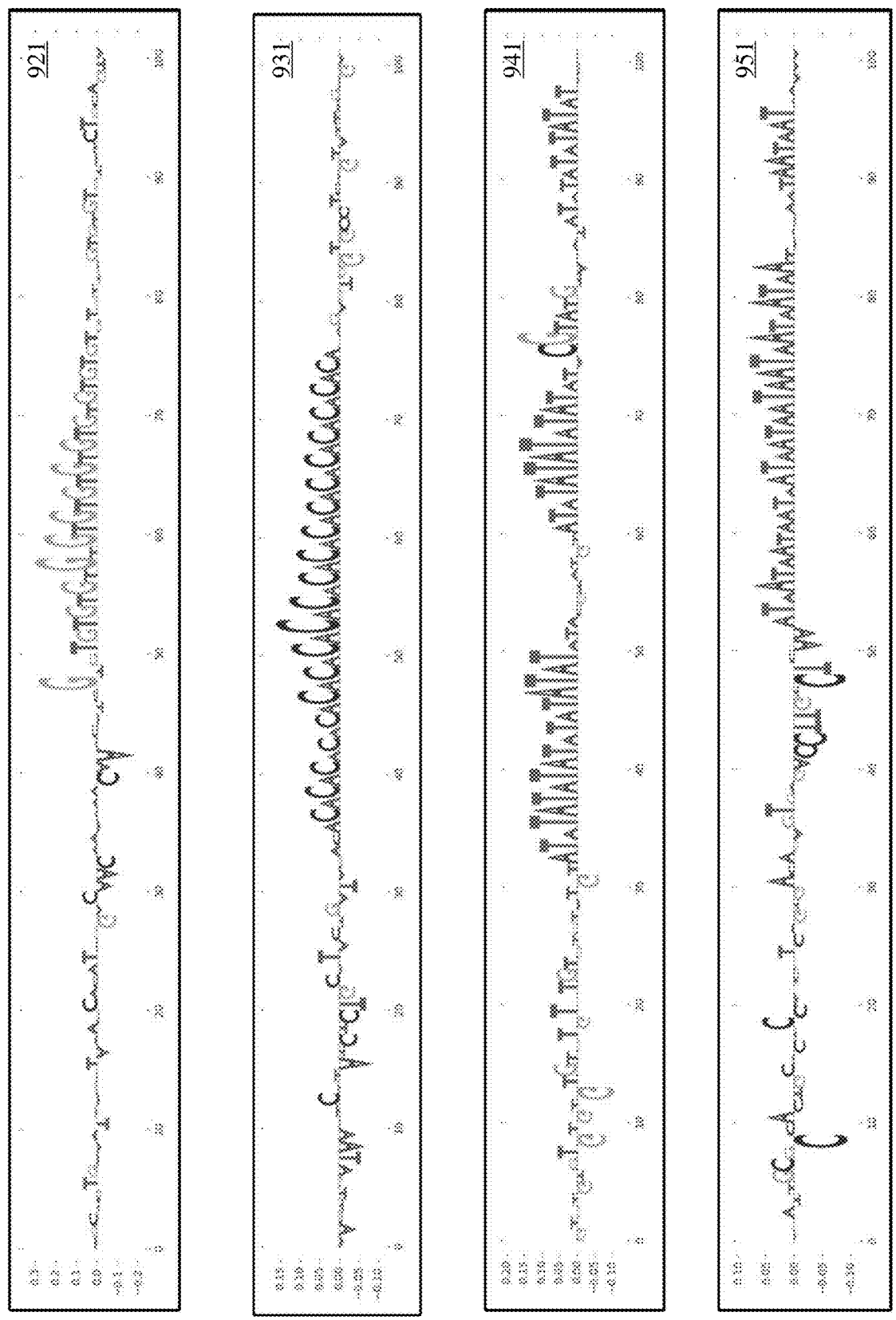
Figure 10C:
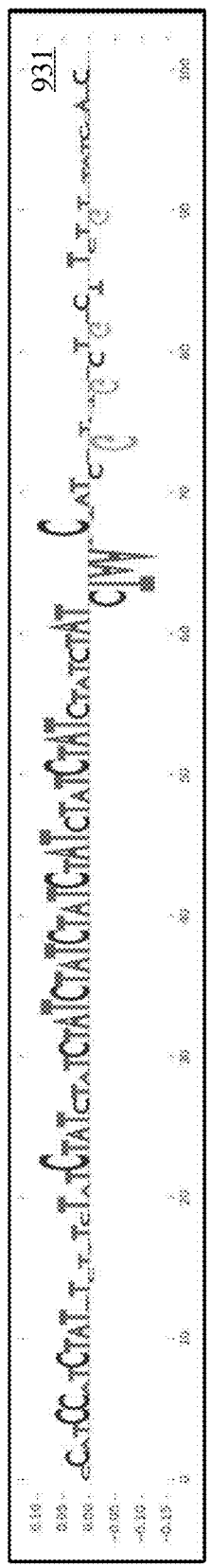
Figure 10C:
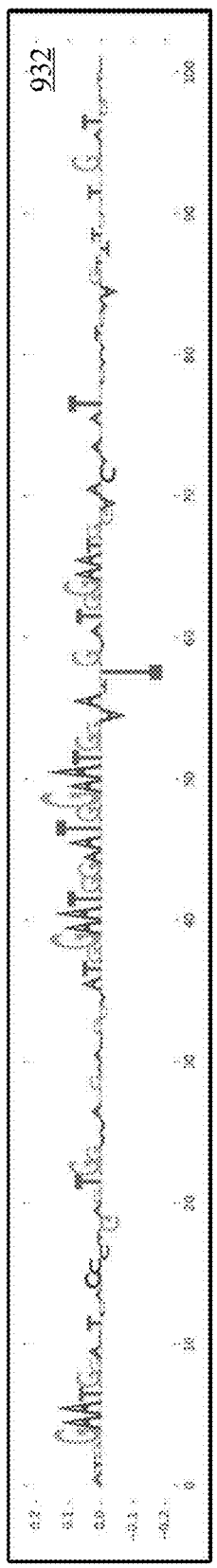
Figure 10C:
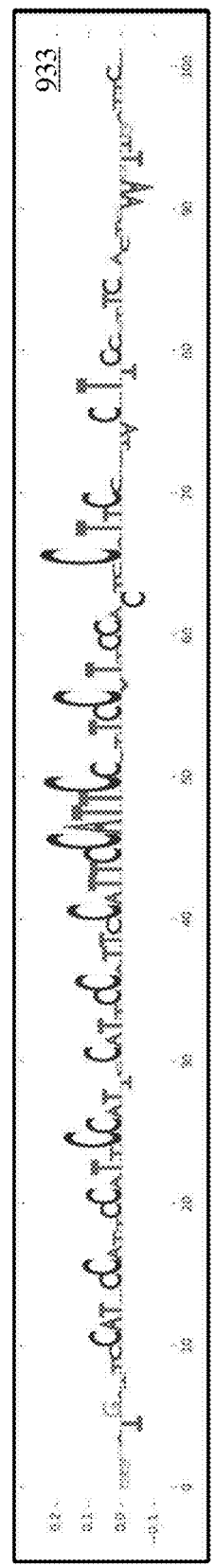
Figure 10C:
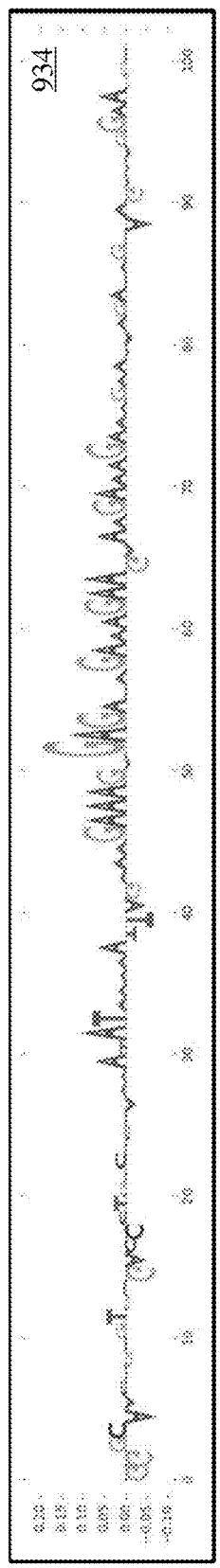

FIGS. 10A to 10C present display of naturally occurring repeat patterns of copolymers in each of the sample nucleotide sequences that contribute to false variant classification. The graphical visualizations presented in FIGS. 10A to 10C are generated using DeepLIFT presented by Shrikumar et. el., in their paper, "Not Just a Black Box: Learning Important Features Through Propagating Activation Differences" available at arxiv.org/pdf/1605.01713.pdf (reference 1). The implementation of the DeepLIFT model is presented at github.com/kundajelab/deeplift (reference 2) and further details for implementing DeepLIFT are presented at biorxiv.org/content/biorxiv/suppl/2017/10/05/105957.DC1/ 105957-6.pdf (reference 3). One or more naturally occurring repeat patterns of copolymers including a variant nucleotide at a target position are given as input to the DeepLIFT model to generate the visualizations shown in FIGS. 10A to 10C. The output of the DeepLIFT model are the arrays of contributions of input to variant classification of a variant nucleotide at the target position.

For example, consider the input sequence shown in the graphical visualization 911. The variant nucleotide 916 is at position 50 in the sample nucleotide sequence comprising of 101 nucleotides. The variant nucleotide at the target position is flanked by at 50 nucleotides on each side at positions 0 to 49 and 51 to 100 in the sample nucleotide sequence. The variant filter 111 of FIG. 2, classified the variant nucleotide ("C") at the target position as a false variant. The output of the DeepLIFT is the visualization 911 showing that the naturally occurring repeat pattern 917 contributed the most to the classification of the variant nucleotide 916. The heights of the nucleotides indicate their respective contributions to the classification of the variant nucleotide. As shown in the graphical visualization 911, the highest contribution is from a sequence of nucleotides 917 which is a repeat pattern comprising a single base "A".

DeepLIFT contribution arrays have the same shape as the input, i.e., input sequence of nucleotides multiplied by 4 for the standard one-hot encoding (presented in FIG. 5). Therefore, DeepLIFT assigns scores to each sequence position by summing over contributions of input neurons associated with a fixed sequence position and associate these summed contributions with the nucleotide present at that position in the input sample nucleotide sequence. The summed contributions are referred to as "DeepLIFT interpretation scores". The following recommended best practices (as presented in reference 3 above) are followed in application of the DeepLIFT model. Contributions of input neurons to the pre-activation (activation before applying final non-linearity) of an output neuron is calculated. When an output layer uses a softmax non-linearity, the weights connecting a fixed penultimate layer neuron to the set of output neurons are mean centered. Because the sample nucleotide sequences are one-hot encoded as shown in FIG. 5, the method of "weight normalization for constrained inputs" is used before converting from Keras to DeepLIFT as described in reference 3 above.

Graphical visualizations 921, 931, and 941 show repeat patterns 927, 934, and 946 respectively, contributing the most to the classification of the variant nucleotide in the sample nucleotide sequences. FIG. 10B includes graphical visualizations 921, 931, 941, and 951. Note that in these graphical visualizations the repeat patterns of copolymers contain patterns of two or more nucleotides. Similarly, FIG. 10C presents more examples of graphical visualizations 931, 932, 933, and 934, illustrating a variety of repeat patterns contributing to the classification of the variant nucleotide at the target position in respective input nucleotide sequences.

Computer System

Figure 11:
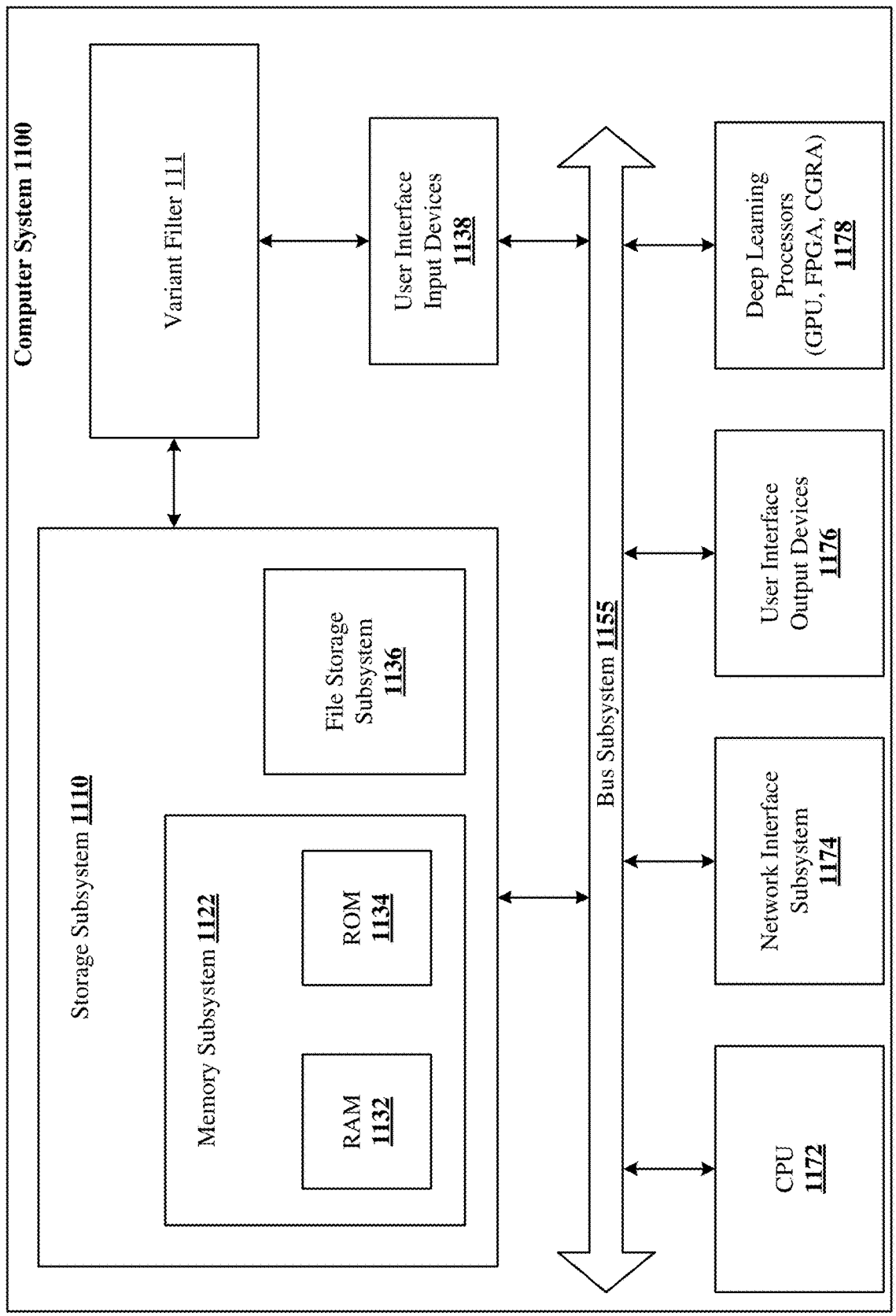
FIG. 11 is a simplified block diagram of a computer system that can be used to implement the variant filter.

FIG. 11 is a simplified block diagram of a computer system 1100 that can be used to implement the variant filter 111 of FIG. 1 for identifying repeat patterns that cause sequence-specific errors. Computer system 1100 includes at least one central processing unit (CPU) 1172 that communicates with a number of peripheral devices via bus subsystem 1155. These peripheral devices can include a storage subsystem 1110 including, for example, memory devices and a file storage subsystem 1136, user interface input devices 1138, user interface output devices 1176, and a network interface subsystem 1174. The input and output devices allow user interaction with computer system 1100. Network interface subsystem 1174 provides an interface to outside networks, including an interface to corresponding interface devices in other computer systems.

In one implementation, the variant filter 111 of FIG. 1 is communicably linked to the storage subsystem 1110 and the user interface input devices 1138.

User interface input devices 1138 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1100.

User interface output devices 1176 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1100 to the user or to another machine or computer system.

Storage subsystem 1110 stores programming and data constructs that provide the functionality of some or all of the modules and methods described herein. Subsystem 1178 can be graphics processing units (GPUs) or field-programmable gate arrays (FPGAs).

Memory subsystem 1122 used in the storage subsystem 1110 can include a number of memories including a main random access memory (RAM) 1132 for storage of instructions and data during program execution and a read only memory (ROM) 1134 in which fixed instructions are stored. A file storage subsystem 1136 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1136 in the storage subsystem 1110, or in other machines accessible by the processor.

Bus subsystem 1155 provides a mechanism for letting the various components and subsystems of computer system 1100 communicate with each other as intended. Although bus subsystem 1155 is shown schematically as a single bus, alternative implementations of the bus subsystem can use multiple busses.

Computer system 1100 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1100 depicted in FIG. 11 is intended only as a specific example for purposes of illustrating the preferred embodiments of the present invention. Many other configurations of computer system 1100 are possible having more or less components than the computer system depicted in FIG. 11.

Sequence-Specific Error (SSE) Correlation

Figure 12:
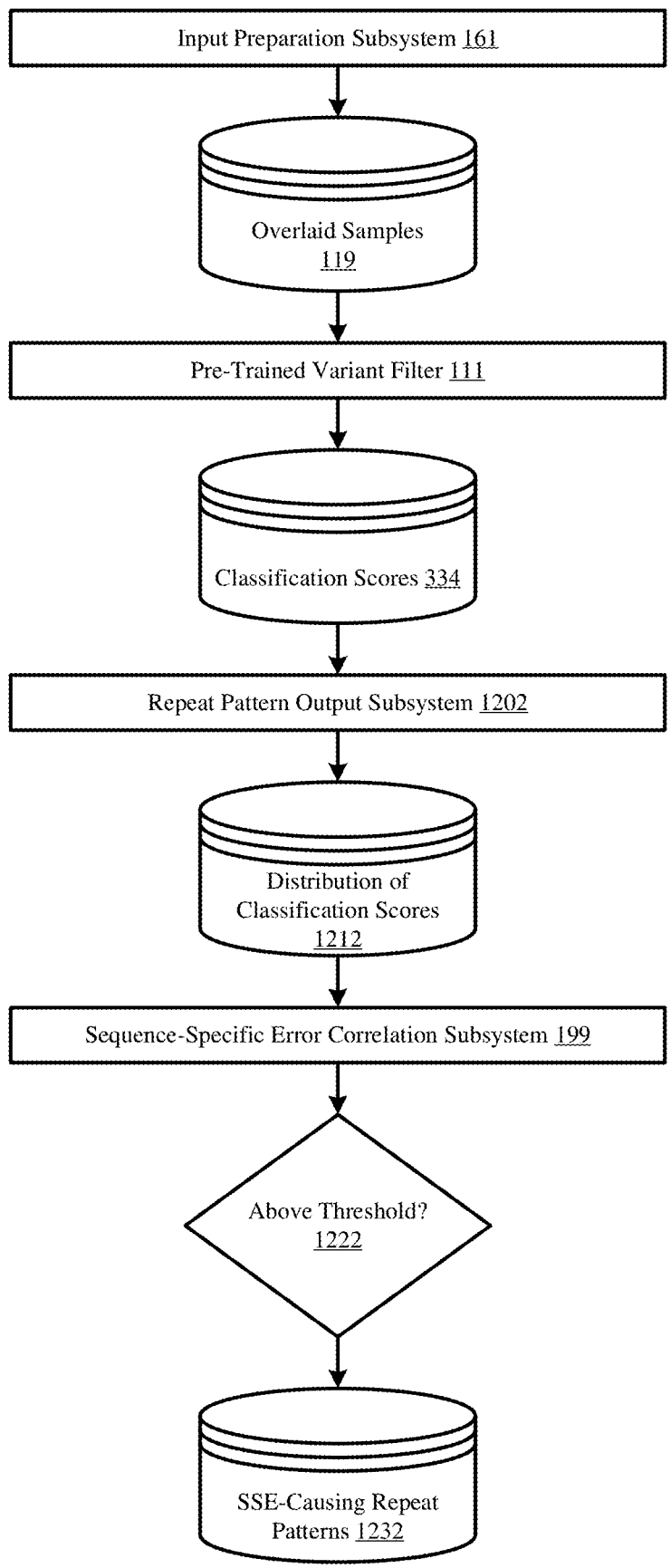
FIG. 12 illustrates one implementation of how sequence-specific errors (SSEs) are correlated to repeat patterns based on false variant classifications.

FIG. 12 illustrates one implementation of how sequence-specific errors (SSEs) are correlated to repeat patterns based on false variant classifications.

The input preparation subsystem 161 computationally overlays the repeat patterns under test on numerous nucleotide sequences and produces the overlaid samples 119. Each repeat pattern represents a particular nucleotide composition that has a particular length and appears in an overlaid sample at a particular offset position. Each overlaid sample has a target position considered to be a variant nucleotide. For each combination of the particular nucleotide composition, the particular length, and the particular offset position, a set of the overlaid samples is computationally generated.

The pre-trained variant filter subsystem 111 processes the overlaid samples 119 through the convolutional neural network 200 and, based on detection of nucleotide patterns in the overlaid samples 119 by convolution filters of the convolutional neural network 200, generates classification scores 334 for likelihood that the variant nucleotide in each of the overlaid samples is a true variant or a false variant.

The repeat pattern output subsystem 1202 outputs distributions 1212 of the classification scores 334 that indicate susceptibility of the pre-trained variant filter subsystem 111 to false variant classifications resulting from presence of the repeat patterns.

The sequence-specific error correlation subsystem 199 specifies, based on a threshold 1222, a subset of the classification scores as indicative of the false variant classifications, and classifies those repeat patterns 1232 which are associated with the subset of the classification scores that are indicative of the false variant classifications as causing the sequence-specific errors. The sequence-specific error correlation subsystem 199 classifies particular lengths and particular offset positions of the repeat patterns 1232 classified as causing the sequence-specific errors as also causing the sequence-specific errors.

FIGS. 7A, 7B, and 7C show an example threshold 702 (e.g., 0.6) that is applied to the outputs distributions 1212 of the classification scores 334 to identify the subset of the classification scores which are above the threshold 702. Such classification scores are indicative of the false variant classifications and repeat patterns associated with them are classified as causing the sequence-specific errors.

Particular Implementations

The technology disclosed relates to identifying repeat patterns that cause sequence-specific errors.

The technology disclosed can be practiced as a system, method, device, product, computer readable media, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A first system implementation of the technology disclosed includes one or more processors coupled to memory. The memory is loaded with computer instructions to identify repeat patterns that cause sequence-specific errors. The system includes an input preparation subsystem running on numerous processors operating in parallel and coupled to memory. The input preparation subsystem overlays repeat patterns under test on nucleotide sequences to produce overlaid samples. Each of the overlaid samples has a variant nucleotide at a target position flanked by at least 20 nucleotides on each side. The repeat patterns are homopolymers of a single base (A, C, G, or T) with at least 6 repeat factors that specify a number of repetitions of the single base in the repeat patterns. The system includes a simulation subsystem that feeds each combination of the repeat patterns overlaid on at least 100 nucleotide sequences in at least 100 overlaid samples to a variant filter for analysis. The system includes a variant filter subsystem, which translates analysis by the variant filter into classification scores for likelihood that the variant nucleotide in each of the overlaid samples is a true variant or a false variant. Finally, the system includes an analysis subsystem that causes display of the classification scores as a distribution for each of the repeat factors to support evaluation of sequence-specific error causation by the repeat patterns.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

In one implementation, the repeat patterns are to right of a center nucleotide in the overlaid samples and not overlapping the center nucleotide. In another implementation, the repeat patterns are to left of a center nucleotide in the overlaid samples and not overlapping the center nucleotide. In another implementation, the repeat patterns include a center nucleotide in the overlaid samples.

The repeat factors are integers in a range of 5 to one-quarter of a count of nucleotides in the overlaid samples. The system is further configured to apply to repeat patterns that are the homopolymers of the single base for each of four bases (A, C, G, and T).

The input preparation subsystem is further configured to produce the repeat patterns and the overlaid samples for the homopolymers for each of the four bases and the analysis subsystem is further configured to cause display of the classification score distribution for each of the homopolymers in juxtaposition.

The repeat patterns are right to a center nucleotide in the overlaid samples and the juxtaposition applies to the homopolymers overlaid right to the center nucleotide. The repeat patterns are left to a center nucleotide in the overlaid samples and the juxtaposition applies to the homopolymers overlaid left to the center nucleotide. The nucleotide sequences on which the repeat patterns are overlaid are randomly generated. The nucleotide sequences on which the repeat patterns are overlaid are randomly selected from naturally occurring DNA nucleotide sequences. The analysis subsystem is further configured to cause display of the classification score distribution for each of the repeat factors using box-and-whisker plots.

The variant filter is trained on at least 500000 training examples of true variants and at least 50000 training examples of false variants. Each training example is a nucleotide sequence with a variant nucleotide at a target position flanked by at least 20 nucleotides on each side. The variant filter is a convolutional neural network (CNN) with two convolutional layers and a fully-connected layer.

Other implementations may include a non-transitory computer readable storage medium storing instructions executable by a processor to perform functions of the system described above. Yet another implementation may include a method performing the functions of the system described above.

A first computer-implemented method implementation of the technology disclosed includes identifying repeat patterns that cause sequence-specific errors. The computer-implemented method includes preparing input by overlaying repeat patterns under test on nucleotide sequences to produce overlaid samples. Each of the overlaid samples has a variant nucleotide at a target position flanked by at least 20 nucleotides on each side. The repeat patterns are homopolymers of a single base (A, C, G, or T) with at least 6 repeat factors that specify a number of repetitions of the single base in the repeat patterns. The computer-implemented method includes feeding each combination of the repeat patterns overlaid on at least 100 nucleotide sequences in at least 100 overlaid samples to a variant filter for analysis. The computer-implemented method includes translating analysis by the variant filter into classification scores for likelihood that the variant nucleotide in each of the overlaid samples is a true variant or a false variant into an output. Finally, the computer-implemented method includes causing display of the classification scores as a distribution for each of the repeat factors to support evaluation of sequence-specific error causation by the repeat patterns.

Each of the features discussed in this particular implementation section for the first system implementation apply equally to this computer-implemented method implementation. As indicated above, all the system features are not repeated here and should be considered repeated by reference.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

Each of the features discussed in this particular implementation section for the system implementation apply equally to this CRM implementation. As indicated above, all the system features are not repeated here and should be considered repeated by reference.

A second system implementation of the technology disclosed includes one or more processors coupled to memory. The memory is loaded with computer instructions to identify repeat patterns that cause sequence-specific errors. The system includes an input preparation subsystem that overlays repeat patterns under test at varying offsets on nucleotide sequences to produce overlaid samples. Each of the overlaid samples has a variant nucleotide at a target position flanked by at least 20 nucleotides on each side. The repeat patterns are homopolymers of a single base (A, C, G, or T) with at least 6 repeat factors that specify a number of repetitions of the single base in the repeat patterns. The varying offsets vary a position at which the repeat patterns are overlaid on the nucleotide sequences. The varying offsets are measurable as an offset between an origin position of the repeat patterns and an origin position of the nucleotide sequences. In one implementation, at least ten offsets are used to produce the overlaid samples.

The system further comprises a simulation subsystem that feeds each combination of the repeat patterns overlaid on at least 100 nucleotide sequences in at least 100 overlaid samples to a variant filter for analysis. The system includes a variant filter subsystem that translates analysis by the variant filter into classification scores for likelihood that the variant nucleotide in each of the overlaid samples is a true variant or a false variant. Finally, the system includes an analysis subsystem that causes display of the classification scores as a distribution for each of the repeat factors to support evaluation of sequence-specific error causation by presence of the repeat patterns at the varying offsets.

Other implementations may include a non-transitory computer readable storage medium storing instructions executable by a processor to perform functions of the system described above. Yet another implementation may include a method performing the functions of the system described above.

A second computer-implemented method implementation of the technology disclosed includes identifying repeat patterns that cause sequence-specific errors. The method includes overlaying repeat patterns under test at varying offsets on nucleotide sequences to produce overlaid samples. Each of the overlaid samples has a variant nucleotide at a target position flanked by at least 20 nucleotides on each side. The repeat patterns are homopolymers of a single base (A, C, G, or T) with at least 6 repeat factors that specify a number of repetitions of the single base in the repeat patterns. The varying offsets vary a position at which the repeat patterns are overlaid on the nucleotide sequences. The offset is measurable as an offset between an origin position of the repeat patterns and an origin position of the nucleotide sequences. In one implementation, at least ten offsets are used to produce the overlaid samples.

The computer-implemented method includes feeding each combination of the repeat patterns overlaid on at least 100 nucleotide sequences in at least 100 overlaid samples to a variant filter for analysis. This is followed by translating analysis by the variant filter into classification scores for likelihood that the variant nucleotide in each of the overlaid samples is a true variant or a false variant. Finally, the computer-implemented method causing display of the classification scores as a distribution for each of the repeat factors to support evaluation of sequence-specific error causation by presence of the repeat patterns at the varying offsets.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

A third system implementation of the technology disclosed includes one or more processors coupled to memory. The memory is loaded with computer instructions to identify repeat patterns that cause sequence-specific errors. The system includes an input preparation subsystem, running on numerous processors operating in parallel and coupled to memory, that overlays repeat patterns under test on nucleotide sequences to produce overlaid samples. Each of the overlaid samples has a variant nucleotide at a target position flanked by at least 20 nucleotides on each side. The repeat patterns are copolymers of at least two bases from four bases (A, C, G, and T) with at least 6 repeat factors that specify a number of repetitions of the at least two bases in the repeat patterns. The system includes a simulation subsystem, running on the numerous processors operating in parallel and coupled to the memory, that feeds each combination of the repeat patterns overlaid on at least 100 nucleotide sequences in at least 100 overlaid samples to a variant filter for analysis. The system includes a variant filter subsystem, running on the numerous processors operating in parallel and coupled to the memory. The variant filter subsystem translates analysis by the variant filter into classification scores for likelihood that the variant nucleotide in each of the overlaid samples is a true variant or a false variant. Finally, the system includes an analysis subsystem, running on the numerous processors operating in parallel and coupled to the memory, that causes display of the classification scores as a distribution for each of the repeat factors to support evaluation of sequence-specific error causation by the repeat patterns.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The repeat patterns are combinatorial enumeration of copatterns of varying repeat factors and varying pattern lengths.

Other implementations may include a non-transitory computer readable storage medium storing instructions executable by a processor to perform functions of the system described above. Yet another implementation may include a method performing the functions of the system described above.

A third computer-implemented method implementation of the technology disclosed includes identifying repeat patterns that cause sequence-specific errors. The method includes overlaying repeat patterns under test on nucleotide sequences to produce overlaid samples. Each of the overlaid samples has a variant nucleotide at a target position flanked by at least 20 nucleotides on each side. The repeat patterns are copolymers of at least two bases from four bases (A, C, G, and T) with at least 6 repeat factors that specify a number of repetitions of the at least two bases in the repeat patterns. The method includes feedings each combination of the repeat patterns overlaid on at least 100 nucleotide sequences in at least 100 overlaid samples to a variant filter for analysis. The method includes translating analysis by the variant filter into classification scores for likelihood that the variant nucleotide in each of the overlaid samples is a true variant or a false variant. Finally, the method includes causing display of the classification scores as a distribution for each of the repeat factors to support evaluation of sequence-specific error causation by the repeat pattern.

Each of the features discussed in this particular implementation section for the third system implementation apply equally to this computer-implemented method implementation. As indicated above, all the system features are not repeated here and should be considered repeated by reference.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

Each of the features discussed in this particular implementation section for the third system implementation apply equally to this CRM implementation. As indicated above, all the system features are not repeated here and should be considered repeated by reference.

A fourth system implementation of the technology disclosed includes one or more processors coupled to memory. The memory is loaded with computer instructions to identify repeat patterns that cause sequence-specific errors. The system includes an input preparation subsystem, running on numerous processors operating in parallel and coupled to memory, that overlays repeat patterns under test at varying offsets on nucleotide sequences to produce overlaid samples. Each of the overlaid samples has a variant nucleotide at a target position flanked by at least 20 nucleotides on each side. The repeat patterns are copolymers of at least two bases from four bases (A, C, G, and T) with at least 6 repeat factors that specify a number of repetitions of the at least two bases in the repeat patterns. The varying offsets vary a position at which the repeat patterns are overlaid on the nucleotide sequences. The varying offsets are measurable as an offset between an origin position of the repeat patterns and an origin position of the nucleotide sequences. In one implementation, at least ten offsets are used to produce the overlaid samples.

The system includes a simulation subsystem, running on the numerous processors operating in parallel and coupled to the memory, that feeds each combination of the repeat patterns. The repeat patterns are overlaid on at least 100 nucleotide sequences in at least 100 overlaid samples to a variant filter for analysis. The system also includes a variant filter subsystem, running on the numerous processors operating in parallel and coupled to the memory, that translates analysis by the variant filter into classification scores for likelihood that the variant nucleotide in each of the overlaid samples is a true variant or a false variant. Finally, the system includes an analysis subsystem running on the numerous processors operating in parallel and coupled to the memory. The analysis subsystem causes display of the classification scores as a distribution for each of the repeat factors to support evaluation of sequence-specific error causation by presence of the repeat patterns at the varying offsets.

Other implementations may include a non-transitory computer readable storage medium storing instructions executable by a processor to perform functions of the system described above. Yet another implementation may include a method performing the functions of the system described above.

A fourth computer-implemented method implementation of the technology disclosed includes identifying repeat patterns that cause sequence-specific errors. The computer-implemented method includes overlaying repeat patterns under test on nucleotide sequences to produce overlaid samples. Each of the overlaid samples has a variant nucleotide at a target position flanked by at least 20 nucleotides on each side. The repeat patterns are copolymers of at least two bases from four bases (A, C, G, and T) with at least 6 repeat factors. The repeat factors specify a number of repetitions of the at least two bases in the repeat patterns. The varying offsets vary a position at which the repeat patterns are overlaid on the nucleotide sequences. The repeat factors are measurable as an offset between an origin position of the repeat patterns and an origin position of the nucleotide sequences. In one implementation, at least ten offsets are used to produce the overlaid samples. The computer-implemented method includes feeding each combination of the repeat patterns overlaid on at least 100 nucleotide sequences in at least 100 overlaid samples to a variant filter for analysis. The computer-implemented method further includes translating analysis by the variant filter into classification scores for likelihood that the variant nucleotide in each of the overlaid samples is a true variant or a false variant. Finally, the computer-implemented method includes causing display of the classification scores as a distribution for each of the repeat factors to support evaluation of sequence-specific error causation by presence of the repeat patterns at the varying offsets.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

A fifth system implementation of the technology disclosed includes one or more processors coupled to memory. The memory is loaded with computer instructions to identify repeat patterns that cause sequence-specific errors. The system includes an input preparation subsystem running on numerous processors operating in parallel and coupled to memory. The input preparation subsystem selects sample nucleotide sequences from natural DNA nucleotide sequences. Each of the sample nucleotide sequences has one or more naturally occurring repeat patterns of copolymers and a variant nucleotide at a target position flanked by at least 20 nucleotides on each side. The system includes a simulation subsystem running on the numerous processors operating in parallel and coupled to the memory. The simulation subsystem feeds each of the sample nucleotide sequences to a variant filter for analysis.

The system includes a variant filter subsystem running on the numerous processors operating in parallel and coupled to the memory. The variant filter subsystem translates analysis by the variant filter into classification scores for likelihood that the variant nucleotide in each of the sample nucleotide sequences is a true variant or a false variant, and makes available activations of parameters of the variant filter responsive to the analysis. Finally, the system include an analysis subsystem running on the numerous processors operating in parallel and coupled to the memory. The analysis subsystem analyzes the activations of the parameters of the variant filter and causes display of a representation of naturally occurring repeat patterns of copolymers in each of the sample nucleotide sequences that contribute to a false variant classification.

Other implementations may include a non-transitory computer readable storage medium storing instructions executable by a processor to perform functions of the system described above. Yet another implementation may include a method performing the functions of the system described above.

A fifth computer-implemented method implementation of the technology disclosed includes identifying repeat patterns that cause sequence-specific errors. The computer-implemented method includes selecting sample nucleotide sequences from natural DNA nucleotide sequences. Each of the sample nucleotide sequences has one or more naturally occurring repeat patterns of copolymers, and a variant nucleotide at a target position flanked by at least 20 nucleotides on each side. The computer-implemented method includes feeding each of the sample nucleotide sequences to a variant filter for analysis. The method includes translating analysis by the variant filter into classification scores for likelihood that the variant nucleotide in each of the sample nucleotide sequences is a true variant or a false variant. The computer-implemented method makes available activations of parameters of the variant filter responsive to the analysis. Finally, the computer-implemented method includes analyzing the activations of the parameters of the variant filter and causing display of a representation of naturally occurring repeat patterns of copolymers in each of the sample nucleotide sequences that contribute to a false variant classification.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

The technology disclosed presents a system for identifying repeat patterns that cause sequence-specific errors.

The system comprises an input preparation subsystem that runs on numerous processors operating in parallel and coupled to memory. The input preparation subsystem overlays repeat patterns under test on nucleotide sequences to produce overlaid samples. Each of the overlaid samples has a variant nucleotide at a target position flanked by at least 20 nucleotides on each side. The repeat patterns include at least one base from four bases (A, C, G, and T) with at least 6 repeat factors.

The system comprises a simulation subsystem that runs on the numerous processors operating in parallel and coupled to the memory. The simulation subsystem feeds each combination of the repeat patterns overlaid on at least 100 nucleotide sequences in at least 100 overlaid samples to a variant filter for analysis.

The system comprises a variant filter subsystem that runs on the numerous processors operating in parallel and coupled to the memory. The variant filter subsystem translates analysis by the variant filter into classification scores for likelihood that the variant nucleotide in each of the overlaid samples is a true variant or a false variant.

The system comprises an analysis subsystem that runs on the numerous processors operating in parallel and coupled to the memory. The analysis subsystem causes display of the classification scores as a distribution for each of the repeat factors to support evaluation of sequence-specific error causation by the repeat patterns.

Each of the features discussed in this particular implementation section for the first system implementation apply equally to this system implementation. As indicated above, all the system features are not repeated here and should be considered repeated by reference.

In one implementation, the repeat patterns are homopolymers of a single base (A, C, G, or T) with the at least 6 repeat factors that specify a number of repetitions of the single base in the repeat patterns.

In another implementation, the repeat patterns are copolymers of at least two bases from four bases (A, C, G, and T) with the at least 6 repeat factors that specify a number of repetitions of the at least two bases in the repeat patterns.

In some implementations, the input preparation subsystem is further configured to overlay the repeat patterns under test at varying offsets on the nucleotide sequences to produce the overlaid samples. The varying offsets vary a position at which the repeat patterns are overlaid on the nucleotide sequences, measurable as an offset between an origin position of the repeat patterns and an origin position of the nucleotide sequences, and at least ten offsets are used to produce the overlaid samples. In such implementations, the analysis subsystem is further configured to cause display of the classification scores as a distribution for each of the repeat factors to support evaluation of sequence-specific error causation by presence of the repeat patterns at the varying offsets.

In one implementation, the repeat patterns are to right of a center nucleotide in the overlaid samples and not overlapping the center nucleotide. In another implementation, the repeat patterns are to left of a center nucleotide in the overlaid samples and not overlapping the center nucleotide. In another implementation, the repeat patterns include a center nucleotide in the overlaid samples.

The repeat factors are integers in a range of 5 to one-quarter of a count of nucleotides in the overlaid samples. The system is further configured to apply to repeat patterns that are the homopolymers of the single base for each of four bases (A, C, G, and T).

The input preparation subsystem is further configured to produce the repeat patterns and the overlaid samples for the homopolymers for each of the four bases and the analysis subsystem is further configured to cause display of the classification score distribution for each of the homopolymers in juxtaposition.

The repeat patterns are right to a center nucleotide in the overlaid samples and the juxtaposition applies to the homopolymers overlaid right to the center nucleotide. The repeat patterns are left to a center nucleotide in the overlaid samples and the juxtaposition applies to the homopolymers overlaid left to the center nucleotide. The nucleotide sequences on which the repeat patterns are overlaid are randomly generated. The nucleotide sequences on which the repeat patterns are overlaid are randomly selected from naturally occurring DNA nucleotide sequences. The analysis subsystem is further configured to cause display of the classification score distribution for each of the repeat factors using box-and-whisker plots.

The variant filter is trained on at least 500000 training examples of true variants and at least 50000 training examples of false variants. Each training example is a nucleotide sequence with a variant nucleotide at a target position flanked by at least 20 nucleotides on each side. The variant filter is a convolutional neural network (CNN) with two convolutional layers and a fully-connected layer.

The technology disclosed presents a computer-implemented method of identifying repeat patterns that cause sequence-specific errors.

The computer-implemented method includes overlaying repeat patterns under test on nucleotide sequences to produce overlaid samples.

The computer-implemented method includes feeding each combination of the repeat patterns overlaid on at least 100 nucleotide sequences in at least 100 overlaid samples to a variant filter for analysis.

The computer-implemented method includes translating analysis by the variant filter into classification scores for likelihood that the variant nucleotide in each of the overlaid samples is a true variant or a false variant.

The computer-implemented method includes causing display of the classification scores as a distribution for each of the repeat factors to support evaluation of sequence-specific error causation by the repeat patterns.

Each of the features discussed in this particular implementation section for the first system implementation apply equally to this computer-implemented method implementation. As indicated above, all the system features are not repeated here and should be considered repeated by reference.

The technology disclosed presents another system for identifying repeat patterns that cause sequence-specific errors in nucleotide sequencing data. The system comprises one or more processors and one or more storage devices storing instructions that, when executed on the one or more processors cause the one or more processors to implement an input preparation subsystem, a variant filter subsystem, and a repeat pattern output subsystem.

The input preparation subsystem is configured to overlay repeat patterns under test on nucleotide sequences to produce overlaid samples. Each of the overlaid samples has a variant nucleotide and the repeat patterns include at least one base from four bases (A, C, G, and T).

The variant filter subsystem is configured to process each combination of the repeat patterns overlaid on the nucleotide sequences in the overlaid samples to generate classification scores for likelihood that the variant nucleotide in each of the overlaid samples is a true variant or a false variant.

The repeat pattern output subsystem is configured to output particular ones of the repeat patterns that cause sequence-specific errors in the nucleotide sequencing data based on the classification scores.

Each of the features discussed in this particular implementation section for the first system implementation apply equally to this system implementation. As indicated above, all the system features are not repeated here and should be considered repeated by reference.

The system is further configured to comprise an analysis subsystem that is configured to cause display of the classification scores as a distribution for each of the repeat factors to support evaluation of sequence-specific error causation by the repeat patterns.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

The technology disclosed presents another system for identifying repeat patterns that cause sequence-specific errors in nucleotide sequencing data. The system comprises one or more processors and one or more storage devices storing instructions that, when executed on the one or more processors cause the one or more processors to implement an input preparation subsystem, a variant filter subsystem, and a repeat pattern output subsystem.

The input preparation subsystem is configured to overlay repeat patterns under test on nucleotide sequences to produce overlaid samples. Each of the overlaid samples has a variant nucleotide and the repeat patterns include at least one base from four bases (A, C, G, and T).

The variant filter subsystem is configured to process each combination of the repeat patterns overlaid on the nucleotide sequences in the overlaid samples to generate classification scores for likelihood that the variant nucleotide in each of the overlaid samples is a true variant or a false variant.

The repeat pattern output subsystem is configured to output particular ones of the repeat patterns that cause sequence-specific errors in the nucleotide sequencing data based on the classification scores.

Each of the features discussed in this particular implementation section for the first system implementation apply equally to this system implementation. As indicated above, all the system features are not repeated here and should be considered repeated by reference.

The system is further configured to comprise an analysis subsystem that is configured to cause display of the classification scores as a distribution for each of the repeat factors to support evaluation of sequence-specific error causation by the repeat patterns.

The technology disclosed presents a computer-implemented method of identifying repeat patterns that cause sequence-specific errors in nucleotide sequencing data.

The computer-implemented method includes overlaying repeat patterns under test on nucleotide sequences to produce overlaid samples. Each of the overlaid samples has a variant nucleotide and the repeat patterns include at least one base from four bases (A, C, G, and T).

The computer-implemented method includes processing each combination of the repeat patterns overlaid on the nucleotide sequences in the overlaid samples through a variant filter subsystem to generate classification scores for likelihood that the variant nucleotide in each of the overlaid samples is a true variant or a false variant.

The computer-implemented method includes translating analysis by the variant filter into classification scores for likelihood that the variant nucleotide in each of the overlaid samples is a true variant or a false variant.

The computer-implemented method includes outputting particular ones of the repeat patterns that cause sequence-specific errors in the nucleotide sequencing data based on the classification scores.

Each of the features discussed in this particular implementation section for the first system implementation apply equally to this computer-implemented method implementation. As indicated above, all the system features are not repeated here and should be considered repeated by reference.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

The technology disclosed presents another system for identifying repeat patterns that cause sequence-specific errors in nucleotide sequencing data. The system comprises one or more processors and one or more storage devices storing instructions that, when executed on the one or more processors cause the one or more processors to implement an input preparation subsystem, a variant filter subsystem, and a repeat pattern output subsystem.

The input preparation subsystem is configured to select sample nucleotide sequences from natural DNA nucleotide sequences. Each of the sample nucleotide sequences has one or more naturally occurring repeat patterns of copolymers and a variant nucleotide.

The variant filter subsystem is configured to process each of the sample nucleotide sequences to generate classification scores for likelihood that the variant nucleotide in each of the sample nucleotide sequences is a true variant or a false variant.

The repeat pattern output subsystem is configured to make available activations of parameters of the variant filter subsystem responsive to the analysis and output particular ones of the repeat patterns that cause sequence-specific errors in the nucleotide sequencing data based upon the classification scores.

Each of the features discussed in this particular implementation section for the first system implementation apply equally to this system implementation. As indicated above, all the system features are not repeated here and should be considered repeated by reference.

The system is further configured to comprise an analysis subsystem that is configured to analyze the activations of the parameters of the variant filter subsystem and cause display of a representation of naturally occurring repeat patterns of copolymers in each of the sample nucleotide sequences that contribute to a false variant classification.

The technology disclosed presents a computer-implemented method of identifying repeat patterns that cause sequence-specific errors in nucleotide sequencing data.

The computer-implemented method includes selecting sample nucleotide sequences from natural DNA nucleotide sequences. Each of the sample nucleotide sequences has one or more naturally occurring repeat patterns of copolymers and a variant nucleotide.

The computer-implemented method includes processing each of the sample nucleotide sequences through a variant filter subsystem to generate classification scores for likelihood that the variant nucleotide in each of the sample nucleotide sequences is a true variant or a false variant.

The computer-implemented method includes making available activations of parameters of the variant filter subsystem responsive to the analysis.

The computer-implemented method includes outputting particular ones of the repeat patterns that cause sequence-specific errors in the nucleotide sequencing data based upon the classification scores.

Each of the features discussed in this particular implementation section for the first system implementation apply equally to this computer-implemented method implementation. As indicated above, all the system features are not repeated here and should be considered repeated by reference.

A computer readable media (CRM) implementation includes a non-transitory computer readable storage medium storing instructions executable by a processor to perform a computer-implemented method as described above. Another CRM implementation may include a system including memory and one or more processors operable to execute instructions, stored in the memory, to perform a computer-implemented method as described above.

Any data structures and code described or referenced above are stored according to many implementations on a computer-readable storage medium, which may be any device or medium that can store code and/or data for use by a computer system. This includes, but is not limited to, volatile memory, non-volatile memory, application-specific integrated circuits (ASICs), field-programmable gate arrays (FPGAs), magnetic and optical storage devices such as disk drives, magnetic tape, CDs (compact discs), DVDs (digital versatile discs or digital video discs), or other media capable of storing computer-readable media now known or later developed.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

CLAUSES

The disclosure also includes the following clauses:

1. A system for identifying repeat patterns that cause sequence-specific errors in nucleotide sequencing data, comprising:

one or more processors and one or more storage devices storing instructions that, when executed on the one or more processors cause the one or more processors to implement:
an input preparation subsystem configured to:
computationally overlay repeat patterns under test on numerous nucleotide sequences and produce overlaid samples,
wherein each repeat pattern represents a particular nucleotide composition that has a particular length and appears in an overlaid sample at a particular offset position,
wherein each overlaid sample has a target position considered to be a variant nucleotide, and
wherein for each combination of the particular nucleotide composition, the particular length, and the particular offset position, a set of the overlaid samples is computationally generated;
a pre-trained variant filter subsystem configured to:
process the overlaid samples through a convolutional neural network and, based on detection of nucleotide patterns in the overlaid samples by convolution filters of the convolutional neural network, generate classification scores for likelihood that the variant nucleotide in each of the overlaid samples is a true variant or a false variant;
a repeat pattern output subsystem configured to:
output distributions of the classification scores that indicate susceptibility of the pre-trained variant filter subsystem to false variant classifications resulting from presence of the repeat patterns; and
a sequence-specific error correlation subsystem configured to:
specify, based on a threshold, a subset of the classification scores as indicative of the false variant classifications, and
classify those repeat patterns which are associated with the subset of the classification scores that are indicative of the false variant classifications as causing the sequence-specific errors.

2. The system of clause 1, wherein the sequence-specific error correlation subsystem is further configured to:
classify particular lengths and particular offset positions of the repeat patterns classified as causing the sequence-specific errors as also causing the sequence-specific errors.

3. The system of any of clauses 1-2, wherein the variant nucleotide is at the target position flanked by at least 20 nucleotides on each side.

4. The system of any of clauses 1-3, wherein the pre-trained variant filter subsystem is configured to process each combination of the repeat patterns overlaid on at least 100 nucleotide sequences in at least 100 overlaid samples.

5. The system of any of clauses 1-5, wherein the repeat patterns include the at least one base from four bases (A, C, G, and T) with at least 6 repeat factors.

6. The system of clause 5, wherein the repeat patterns are homopolymers of a single base (A, C, G, or T) with the at least 6 repeat factors; and wherein the at least 6 repeat factors specify a number of repetitions of the single base in the repeat patterns.

7. The system of any of clauses 1-6, wherein the repeat patterns are copolymers of at least two bases from four bases (A, C, G, and T) with the at least 6 repeat factors; and wherein the at least 6 repeat factors specify a number of repetitions of the at least two bases in the repeat patterns.

8. The system of any of clauses 1-7, wherein the offset positions vary in terms of a position at which the repeat patterns are overlaid on the nucleotide sequences, measurable as an offset between an origin position of the repeat patterns and an origin position of the nucleotide sequences, and at least ten offsets are used to produce the overlaid samples.

9. The system of any of clauses 1-8, wherein the repeat patterns are to right of a center nucleotide in the overlaid samples and not overlapping the center nucleotide.

10. The system of any of clauses 1-9, wherein the repeat patterns are to left of a center nucleotide in the overlaid samples and not overlapping the center nucleotide.

11. The system of any of clauses 1-10, wherein the repeat patterns include a center nucleotide in the overlaid samples.

12. The system of any of clauses 1-11, wherein the repeat factors are integers in a range of 5 to one-quarter of a count of nucleotides in the overlaid samples.

13. The system of clause 6, further configured to apply to repeat patterns that are the homopolymers of the single base for each of four bases (A, C, G, and T).

14. The system of clause 13, wherein the input preparation subsystem is further configured to produce the repeat patterns and the overlaid samples for the homopolymers for each of the four bases.

15. The system of clause 14, wherein the repeat patterns are right to a center nucleotide in the overlaid samples and the juxtaposition applies to the homopolymers overlaid right to the center nucleotide.

16. The system of clause 14, wherein the repeat patterns are left to a center nucleotide in the overlaid samples and the juxtaposition applies to the homopolymers overlaid left to the center nucleotide.

17. The system of any of clauses 1-16, wherein the nucleotide sequences on which the repeat patterns are overlaid are randomly generated.

18. The system of any of clauses 1-17, wherein the nucleotide sequences on which the repeat patterns are overlaid are randomly selected from naturally occurring DNA nucleotide sequences.

19. The system of any of clauses 1-18, wherein an analysis subsystem is configured to cause display of the distributions of the classification scores for each of the repeat factors.

20. The system of any of clauses 1-19, wherein the pre-trained variant filter subsystem is trained on at least 500000 training examples of true variants and at least 50000 training examples of false variants; and
wherein each training example is a nucleotide sequence with a variant nucleotide at a target position flanked by at least 20 nucleotides on each side.

21. The system of any of clauses 1-20, wherein the pre-trained variant filter subsystem has convolutional layers, a fully-connected layer, and a classification layer.

22. A computer-implemented method of identifying repeat patterns that cause sequence-specific errors in nucleotide sequencing data, including:
computationally overlaying repeat patterns under test on numerous nucleotide sequences and producing overlaid samples, wherein each repeat pattern represents a particular nucleotide composition that has a particular length and appears in an overlaid sample at a particular offset position, wherein each overlaid sample has a target position considered to be a variant nucleotide, and wherein for each combination of the particular nucleotide composition, the particular length, and the particular offset position, a set of the overlaid samples is computationally generated;

processing the overlaid samples through a convolutional neural network and, based on detection of nucleotide patterns in the overlaid samples by convolution filters of the convolutional neural network, generating classification scores for likelihood that the variant nucleotide in each of the overlaid samples is a true variant or a false variant;

outputting distributions of the classification scores that indicate susceptibility of the pre-trained variant filter subsystem to false variant classifications resulting from presence of the repeat patterns; and specifying, based on a threshold, a subset of the classification scores as indicative of the false variant classifications and classifying those repeat patterns which are associated with the subset of the classification scores that are indicative of the false variant classifications as causing the sequence-specific errors.

23. The computer-implemented method of clause 22, implementing each of the clauses which ultimately depend from clause 1.

24. A non-transitory computer readable storage medium impressed with computer program instructions to identify repeat patterns that cause sequence-specific errors in nucleotide sequencing data, the instructions, when executed on a processor, implement a computer-implemented method comprising:

computationally overlaying repeat patterns under test on numerous nucleotide sequences and producing overlaid samples, wherein each repeat pattern represents a particular nucleotide composition that has a particular length and appears in an overlaid sample at a particular offset position, wherein each overlaid sample has a target position considered to be a variant nucleotide, and wherein for each combination of the particular nucleotide composition, the particular length, and the particular offset position, a set of the overlaid samples is computationally generated;

processing the overlaid samples through a convolutional neural network and, based on detection of nucleotide patterns in the overlaid samples by convolution filters of the convolutional neural network, generating classification scores for likelihood that the variant nucleotide in each of the overlaid samples is a true variant or a false variant;

outputting distributions of the classification scores that indicate susceptibility of the pre-trained variant filter subsystem to false variant classifications resulting from presence of the repeat patterns; and specifying, based on a threshold, a subset of the classification scores as indicative of the false variant classifications and classifying those repeat patterns which are associated with the subset of the classification scores that are indicative of the false variant classifications as causing the sequence-specific errors.

25. The non-transitory computer readable storage medium of clause 24, implementing each of the clauses which ultimately depend from clause 1.

What is claimed is:

1. A system for identifying repeat patterns that cause sequence-specific errors in nucleotide sequencing data corresponding to one or more biological samples, comprising:

one or more processors and one or more storage devices storing instructions that, when executed on the one or more processors, cause the one or more processors to implement:

an input preparation subsystem operatively coupled to a sequencer instrument and configured to:
identify nucleotide sequences corresponding to the one or more biological samples;
computationally overlay repeat patterns under test on the nucleotide sequences and produce overlaid samples,
wherein each repeat pattern represents a particular nucleotide composition that has a particular length and appears in an overlaid sample at a particular offset position, wherein each overlaid sample has a target position considered to be a variant nucleotide, and
wherein for each combination of the particular nucleotide composition, the particular length, and the particular offset position, a set of the overlaid samples is computationally generated;

a variant filter subsystem operatively coupled to the sequencer instrument and configured to:
process the overlaid samples through a convolutional neural network and, based on detection of nucleotide patterns in the overlaid samples by convolution filters of the convolutional neural network, generate classification scores for likelihood that the variant nucleotide in each of the overlaid samples is a true variant or a false variant;

a repeat pattern output subsystem operatively coupled to the sequencer instrument and configured to:
output distributions of the classification scores that indicate susceptibility of the variant filter subsystem to false variant classifications resulting from presence of the repeat patterns; and a sequence-specific error correlation subsystem operatively coupled to the sequencer instrument and configured to:
specify, based on a threshold, a subset of the classification scores as indicative of the false variant classifications, and
classify those repeat patterns which are associated with the subset of the classification scores that are indicative of the false variant classifications as causing the sequence-specific errors in the nucleotide sequencing data corresponding to the one or more biological samples.

2. The system of claim 1, wherein the sequence-specific error correlation subsystem is further configured to:
classify particular lengths and particular offset positions of the repeat patterns classified as causing the sequence-specific errors as also causing the sequence-specific errors.

3. The system of claim 1, wherein the variant nucleotide is at the target position flanked by at least 20 nucleotides on each side.

4. The system of claim 1, wherein the variant filter subsystem is configured to process each combination of the repeat patterns overlaid on at least 100 nucleotide sequences in at least 100 overlaid samples.

5. The system of claim 1, wherein the repeat patterns include at least one base from four bases (A, C, G, and T) with at least 6 repeat factors, wherein the at least 6 repeat factors specify a number of repetitions of the at least one base from the four bases in the repeat patterns.

6. The system of claim 5, wherein the repeat patterns are homopolymers of a single base (A, C, G, or T) with the at least 6 repeat factors, wherein the at least 6 repeat factors specify a number of repetitions of the single base in the repeat patterns.

7. The system of claim 1, wherein the repeat patterns include the variant nucleotide at a target position in the overlaid samples.

8. The system of claim 7, wherein the input preparation subsystem is further configured to produce the repeat patterns and the overlaid samples for the homopolymers for each of the four bases.

9. The system of claim 8, wherein the repeat patterns are right to a center nucleotide in the overlaid samples, and a juxtaposition applies to the homopolymers overlaid right to the center nucleotide.

10. The system of claim 8, wherein the repeat patterns are left to a center nucleotide in the overlaid samples, and a juxtaposition applies to the homopolymers overlaid left to the center nucleotide.

11. The system of claim 1, wherein the nucleotide sequences on which the repeat patterns are overlaid are randomly generated.

12. The system of claim 5, wherein the at least 6 repeat factors are integers in a range of 5 to one-quarter of a count of nucleotides in the overlaid samples.

13. The system of claim 5, wherein the repeat patterns are copolymers of at least two bases from four bases (A, C, G, and T) with the at least 6 repeat factors, and wherein the at least 6 repeat factors specify a number of repetitions of the at least two bases in the repeat patterns.

14. The system of claim 1, wherein particular offset positions of the repeat patterns vary in terms of a position at which the repeat patterns are overlaid on the nucleotide sequences, measurable as an offset between an origin position of the repeat patterns and an origin position of the nucleotide sequences, and at least ten offsets are used to produce the overlaid samples.

15. The system of claim 1, wherein the repeat patterns are to right of the variant nucleotide at a target position in the overlaid samples and not overlapping the variant nucleotide.

16. The system of claim 1, wherein the repeat patterns are to left of the variant nucleotide at a target position in the overlaid samples and not overlapping the variant nucleotide.

17. The system of claim 1, wherein the nucleotide sequences on which the repeat patterns are overlaid are randomly selected from naturally occurring DNA nucleotide sequences.

18. The system of claim 5, wherein the repeat pattern output subsystem is configured to cause display of the output distributions of the classification scores for each of the at least 6 repeat factors.

19. The system of claim 6, further configured to apply to repeat patterns that are the homopolymers of the single base for each of four bases (A, C, G, and T).

20. The system of claim 1, wherein the variant filter subsystem trains on at least 500000 training examples of true variants and at least 50000 training examples of false variants, wherein each training example is a nucleotide sequence with a variant nucleotide at a target position flanked by at least 20 nucleotides on each side.

21. The system of claim 1, wherein the variant filter subsystem has convolutional layers, a fully-connected layer, and a classification layer.

22. A computer-implemented method of identifying repeat patterns that cause sequence-specific errors in nucleotide sequencing data corresponding to one or more biological samples, including:
   identifying, by an input preparation subsystem operatively coupled to a sequencer instrument, nucleotide sequences corresponding to the one or more biological samples;
   computationally overlaying, by the input preparation subsystem, repeat patterns under test on the nucleotide sequences and producing overlaid samples,
      wherein each repeat pattern represents a particular nucleotide composition that has a particular length and appears in an overlaid sample at a particular offset position,
      wherein each overlaid sample has a target position considered to be a variant nucleotide, and
      wherein for each combination of the particular nucleotide composition, the particular length, and the particular offset position, a set of the overlaid samples is computationally generated;
   processing, by a variant filter subsystem operatively coupled to the sequencer instrument, the overlaid samples through a convolutional neural network and, based on detection of nucleotide patterns in the overlaid samples by convolution filters of the convolutional neural network, generating classification scores for likelihood that the variant nucleotide in each of the overlaid samples is a true variant or a false variant;
   outputting, by a repeat pattern output subsystem operatively coupled to the sequencer instrument, distributions of the classification scores that indicate susceptibility of the variant filter subsystem to false variant classifications resulting from presence of the repeat patterns; and
   specifying, by a sequence-specific error correlation subsystem operatively coupled to the sequencer instrument and based on a threshold, a subset of the classification scores as indicative of the false variant classifications; and
   classifying, by the sequence-specific error correlation subsystem, those repeat patterns which are associated with the subset of the classification scores that are indicative of the false variant classifications as causing the sequence-specific errors in the nucleotide sequencing data corresponding to the one or more biological samples.

23. A non-transitory computer readable storage medium impressed with computer program instructions to identify repeat patterns that cause sequence-specific errors in nucleotide sequencing data corresponding to one or more biological samples, the computer program instructions, when executed on a processor, implement actions comprising:
   identifying, by an input preparation subsystem operatively coupled to a sequencer instrument, nucleotide sequences corresponding to the one or more biological samples;
   computationally overlaying, by the input preparation subsystem, repeat patterns under test on the nucleotide sequences and producing overlaid samples,
      wherein each repeat pattern represents a particular nucleotide composition that has a particular length and appears in an overlaid sample at a particular offset position,
      wherein each overlaid sample has a target position considered to be a variant nucleotide, and
      wherein for each combination of the particular nucleotide composition, the particular length, and the particular offset position, a set of the overlaid samples is computationally generated;
   processing, by a variant filter subsystem operatively coupled to the sequencer instrument, the overlaid samples through a convolutional neural network and, based on detection of nucleotide patterns in the overlaid samples by convolution filters of the convolutional neural network, generating classification scores for likelihood that the variant nucleotide in each of the overlaid samples is a true variant or a false variant;

outputting, by a repeat pattern output subsystem operatively coupled to the sequencer instrument, distributions of the classification scores that indicate susceptibility of the variant filter subsystem to false variant classifications resulting from presence of the repeat patterns; and specifying, by a sequence-specific error correlation subsystem operatively coupled to the sequencer instrument and based on a threshold, a subset of the classification scores as indicative of the false variant classifications; and classifying, by the sequence-specific error correlation subsystem, those repeat patterns which are associated with the subset of the classification scores that are indicative of the false variant classifications as causing the sequence-specific errors in the nucleotide sequencing data corresponding to the one or more biological samples.

* * * * *